United States Patent [19]
Domenico

[11] Patent Number: 6,086,921
[45] Date of Patent: Jul. 11, 2000

[54] METAL/THIOL BIOCIDES

[75] Inventor: Philip Domenico, Elmhurst, N.Y.

[73] Assignee: Wintrop-University Hospital, Mineola, N.Y.

[21] Appl. No.: 08/960,031

[22] Filed: Oct. 28, 1997

Related U.S. Application Data

[63] Continuation-in-part of application No. 08/883,584, Jun. 26, 1997, Pat. No. 5,928,671, which is a continuation of application No. 08/428,464, Apr. 25, 1995, abandoned.

[51] Int. Cl.$^7$ .......................... A01N 59/02; A01N 59/16; A61K 33/04; A61K 33/24
[52] U.S. Cl. .......................... 424/653; 504/152; 514/345; 514/706
[58] Field of Search .................................. 424/629, 651, 424/653; 514/706, 363, 345; 504/152

[56] References Cited

U.S. PATENT DOCUMENTS

| | | | |
|---|---|---|---|
| 2,809,971 | 10/1957 | Bernstein et al. | 260/270 |
| 3,429,905 | 2/1969 | Mosby | 260/429.7 |
| 3,558,783 | 1/1971 | Leebrick et al. | 424/296 |
| 3,583,999 | 6/1971 | Damico | 260/294.8 |
| 3,753,990 | 8/1973 | Curry | 260/270 |
| 3,773,770 | 11/1973 | Damico | 260/290 |
| 3,833,565 | 9/1974 | Curry | 260/270 |
| 3,852,441 | 12/1974 | Kooistra, Jr. | 424/245 |
| 3,890,242 | 6/1975 | Curry | 252/107 |
| 4,374,825 | 2/1983 | Bolich, Jr. et al. | 424/70 |
| 4,474,760 | 10/1984 | Hill | 424/174 |
| 4,524,110 | 6/1985 | Heeres et al. | 428/537.1 |
| 4,963,344 | 10/1990 | Gries et al. | 424/9 |
| 5,104,645 | 4/1992 | Cardin et al. | 424/70 |
| 5,541,233 | 7/1996 | Roenigk | 521/54 |
| 5,593,670 | 1/1997 | Trinh et al. | 424/76.1 |
| 5,596,102 | 1/1997 | Austin | 548/101 |
| 5,605,681 | 2/1997 | Trandai et al. | 424/65 |
| 5,624,666 | 4/1997 | Coffindaffer et al. | 424/70.21 |
| 5,643,971 | 7/1997 | Roenigk | 523/122 |

FOREIGN PATENT DOCUMENTS 9412034  6/1994  WIPO .

OTHER PUBLICATIONS

W. Beil et al., Pharmacology 47:135–140 (1993).
W. Beil et al., Pharmacology 47:141–144 (1993).
W. Beil et al., Pharmacology 50:333–337 (1995).
D.W. Bierer, Rev. Infect. Dis. 12(1):S3–S8 (1990).
D. Chaleil et al., J. Inorg. Biochem. 15:213–221 (1981).
N. Chiba et al., Am. J. Gastroenterol. 87(12):1716–1727 (1992).
N.A. Cornick et al., Rev. Infec. Dis. 12(1):S9–S10 (1990).
J.S. Dixon, Scand. J. Gastroenterol. 30(212):48–62 (1995).
P. Domenico et al., J. Antimicro. Chemo. 28:801–810 (1991).
P. Domenico et al., Infection 20(2):18/66–23/71 (1992).
P. Domenico et al., Eur. J. Clin. Microbiol. Infec. Dis. 11:170–175 (1992).

P. Domenico et al., "Synergistic Inhibitory Effects of Bismuth and Dimercaprol Against Gram–Negative Bacteria," 6th Int. Cong. for Infec. Dis., Prague (Apr. 26, 1994).
P. Domenico et al., "Mechanism of Bismuth–Dimercaprol Antimicrobial Snyergy," 34th ICAAC, Florida (Oct. 1994).
P. Domenico et al., "Bismuth–Dimercaprol Chelate: A Potent, New Antimicrobial Agent," Abstract (Oct. 1994).
P. Domenico, "Comparative Antibacterial Properties of Bismuth–Dimercaprol and Chlorhexidine," 95th Gen'l. Meeting Amer. Soc. Microbiol., Washington, D.C. (May 1995).
P. Domenico et al., "Bismuth–Dimercaprol Activity Against Multiply Resistant Gram–Positive Bacteria," Clin. Res. Meeting, Abstract (May. 1995).
P. Domenico et al., In vitro Antifungal Activities of BisBAL and BisME, Two Thiol–Chelated Bismuth Compounds, 36th ICAAC, Abstract F188 (Sep. 1996).
P. Domenico et al., "Efficacy/Toxicity of Bismuth–Dimercaprol in a Burn Wound Sepsis Model," 9th ASM General Meeting, Abstract A10 (May 1996).
P. Domenico et al., "Antimicrobial Activity of the Bismuth–Thiol Chelates, BisBAL and BisME," Clin. Res. 44:332A, Abstract (1996).
P. Domenico et al., Annals of N.Y. Acad. Sci. 797:269–270 (1996).
P. Domenico et al., Antimicrob. Agents and Chemo. 38(6):1031–1040 (1997).
P. Domenico et al., Antimicrob. Agents and Chemo. 41(8):1697–1703 (1997).
P. Domenico et al., "Potentiation of Bismuth Antibacterial Activity by Thiol Chelators," 97th ASM Gen'l Meeting, Florida, Official Abstract Form & Abstract A–43 (May 1997).
B.E. Douglas et al., Concepts and Models of Inorganic Chem., 3rd Ed. pp. 463–465 1994).
H.L. DuPont et al., New Eng. J. Med. 328:1821–1827 (1993).
D. Figueroa–Quintanilla et al., New Eng. J. Med. 328(23):1653–1658 (1993).
S.L. Gorbach et al., Reviews of Infec. Dis. 12(1):S21–S23 (1990).
Gould et al., "Activity of the Novel Compounds BisBAL and BisME Against *Burkholderia cepacia*," 36th ICAAC, Louisiana, Abstract F246 (1996).
D.Y. Graham et al., Ann. Intern. Med. 115:266–269 (1991).
D.Y. Graham et al., Gastroenterol. 102:493–496 (1992).
W. Hespe et al., Gastroenterol. 104(4):1242–1243 (1993).
R. Husseini et al., Microbios 29(116):109–125 (1980).

(List continued on next page.)

*Primary Examiner*—Phyllis G. Spivack
*Attorney, Agent, or Firm*—Ostrolenk, Faber, Gerb & Soffen, LLP

[57] ABSTRACT

A composition described wherein bismuth is chelated by a complexing agent such as a pyrithione or certain other thiol compounds in the form a metal:complexing agent complex. Methods for using the composition as a bacteriocidal, bacteriostatic, antibiofilm, antifungal, and antiviral agent and as a disinfectant and preservative are also provided.

41 Claims, 4 Drawing Sheets

OTHER PUBLICATIONS

R. Iffland, "Bismuth" in *Metals in Clinical and Analytical Chemistry*, Marcel Dekker, Inc. Chap. 21, pp. 269–281 (1994).

T. Klapötke, Biol. Metals 1:69–76 (1988).

M.D. Manhart, Reviews of Infec. Dis. 12(1):S11–S15 (1990).

B.J. Marshall, Reviews of Infec. Dis. 12(1):S87–S93 (1990).

Molina et al., Acta. Neurol. Scand. 79:200–203 (1989).

Molina et al., Med. Clínicas 93(1):20–22 (1989).

G.L. Newton et al., Methods of Enzymology, vol. 251, pp. 148–166, Academic Press (1995).

P–M. Roy et al., The Lancet 344:1708 (1994).

K.W. Shea et al., "Vancomycin Resistant Enterococci (VRE) Colonization in an Outpatient Hemodialysis (HD) Unit," 6th Ann. Mtg. of the Soc. for Healthcare Epidemiology of America, Official Abstract Form (Apr. 1996).

A. Slikkerveer et al., Med. Toxicol. Adverse Drug. Exp. 4(5):303–323 (1989).

A.J. Wagstaff et al., Drugs 36:132–157 (1988).

A.P.R. Wilson, The Lancet 344:1313–1314 (1994).

"The Pharmacological Basis of Therapeutics, Heavy Metal Antagonists, Halogens and Halogen–Containing Compounds," 7th Ed., Goodman & Gilman, pp. 963–964 and 1621–1622 (1985).

Klapoetke, T., J. Organomet. Chem. 331(3), 299–307 (abstract), 1987.

L. Agocs et al., "Spectroscopic, Structural, and Mass Spectrometric Studies on Two Systematic Series of Dithiabismuth (III) Heterocycles: Identification of Bismuthenium Cations and Their Solvent Complexes," J. Am. Chem. Soc. 118:3225–3232 (1996).

L. Agocs et al., "The Structurally Flexible Bicyclic Bis(2–hydroxyethanethiolato)bismuth (III) Complex: A Model for Assymetric Monoanionic Chelation of Bismuth (III)," Inorg. Chem. 36:2855–2860 (1997).

E. Asato et al., "Bismuth (III) Complexes of 2–Mercaptoethanol: Preparation, Structural and Spectroscopic Characterization, Antibactericidal Activity Toward *Helicobacter pylori*, and Inhibitory Effect Toward *H. pylory*–Produced Urease," Bull. Chem. Soc. Jpn. 70:639–648 (1997).

N. Burford et al., "Anti–*Helicobacter Pylori* Properties of New Bismuth Compounds," Digestive Disease Week and the 95th Ann. Mtg. of the American Gastroenterological Association, May 15–18, 1994, New Orleans, Louisiana; Supplement to Gastroenterology 06(4):A59 (1994).

R. Diemer et al., "Preparation and Characterization of Biologically Active Bismuth (III) Tropolonato Complexes," Chem. Ber. 128:335–342 (1995).

U. Dittes et al., "Overview on Bismuth (III) and Bismuth (V) Complexes with Activity Against *Helicobacter pylori*," Coordination Chem. Rev. 163:345–364 (1997).

E.A.H. Friedheim, "Dimercapto Derivatives of Metal–Containing Compounds," Chemical Abstract vol. 49, Abstract at column 12530 (1955).

E.A.H. Friedheim, "Heterocyclic Organomeallic Compounds," Chemical Abstract vol. 49, Abstract at column 1815 (1955).

E.A.H. Friedheim, "Therapeutically Active Bismuth Organic Compounds," Chemical Abstract vol. 49, Abstract at column 15946 (1955).

R. LaBlanc et al., "The Efficacy of Novel Bismuth (Bi) Compounds in Healing Gastric Ulceration in the Rat Varies with Chemical Structure: Implications for *Helicobacter Pylor* (HP) Treatment, " AGA Abstracts, Gastroenterology 108(4):A860 (1995).

D.E. Mahony et al., "Antimicrobial Activity of Synthesized Bismuth Compounds on *Clostridium difficile*," Abstract presented at the 64th Conjoint Meeting on Infec. Dis. Ontario, Nov. 10–14, 1996.

D.E. Mahony et al., "Antimicrobial Activity of Synthesized Bismuth Compounds on *Clostridium difficile*," Abstract presented at the 2nd Int'l Mtg. on the Molecular Genetics and Pathogenesis of the Clostridia, France, Jun. 22–25, 1997.

P. Powell, "Some Dithiolato–Derivatives, and Theoretical Chemistry," J. Chem. Soc. (A) 11:2587–2588 (1968).

METAL/THIOL BIOCIDES

This application is a continuation-in-part of U.S. application Ser. No. 08/883,584, filed Jun. 26, 1997, which is a continuation U.S. application Ser. No. 08/428,464, filed Apr. 25, 1995, now abandoned.

FIELD OF THE INVENTION

The present invention relates to a composition and a method for the amelioration and inhibition of bacterial, viral and other microbial activity, and more particularly, to certain metal:thiol complexes and metal/thiol mixtures, and their uses. Bacteriocidal and bacteriostatic properties are demonstrated, as are anti-biofilm properties. The present invention also relates to anti-biofilm use of certain metal:pyrithione complexes and metal/pyrithione mixtures.

DESCRIPTION OF THE RELATED ART

Infectious diseases of the digestive tract constitute a major health problem throughout the world. Infectious diarrheal disease is one of the leading causes of morbidity and mortality in developing countries. In developed countries, diarrhea and colitis are frequent symptoms during antibiotic therapy. Food contamination with Salmonella, Shigella, Campylobacter, or *E. coli* poses a major health problem. Diarrhea is the most frequent discomfort among travelers. Even ulcers are now considered an infectious disease.

The finding in 1983 that *Helicobacter pylori* was the probable cause of ulcers has precipitated intense activity in developing therapies to eradicate this organism from the gastro-intestinal (GI) tract. Therapies have emerged, involving combinations of antibiotics, $H_2$-inhibitors and bismuth compounds. These therapies rely heavily on bismuth to prevent recurrence. At present, the preferred form to administer bismuth is as the subcitrate (colloidal bismuth subcitrate or CBS) or as the subsalicylate (BSS, available commercially as Pepto-Bismol®).

The mechanisms by which colloidal bismuth subcitrate or Bismuth subsalicylate help to eradicate *H. pylori* are not fully understood and are currently under investigation. For a review of the properties of colloidal bismuth subcitrate, see Wagstaff, et al., Drugs 36:132–157 (1988). Apparently no single mechanism of bismuth activity can account for all of the anti-ulcer effects suggested in the literature. Indeed a number of therapeutic activities may be involved. Experiments recently performed by Beil et. al., Pharmacology; 47:135–140 (1993) investigated the interactions between colloidal bismuth subcitrate (CBS) and sulfhydryls and their results indicated that dithiothreitol did not enhance the antibacterial activity of colloidal bismuth subcitrate.

Bismuth compounds are also used in numerous other medical applications. For example, they are used orally as anti-diarrheal agents, for an upset stomach, nausea, vomiting, and as an internal deodorant, and as skin antiseptics. Bismuth compounds are also used prophylactically for Traveler's diarrhea, and as an iodoform paraffin paste, they are used to limit infection of surgical wounds. In general, bismuth has antibacterial properties with proven medical usefulness. However, the potency of bismuth compounds is relatively low, especially when iron is present. In addition, one of the major problems with using bismuth is its insolubility in aqueous solutions.

Bismuth also has selective effects on expression of virulence factors in bacteria. Concentrations below that which inhibited bacterial growth nevertheless repressed the expression of capsular polysaccharide (CPS) from *K. pneumoniae* and other members of its family Enterobacteriaciae. It also represses the expression of certain pill involved in adherence. The antibacterial potency of bismuth is especially strong under low iron conditions. Increasing iron negates the inhibitory effects of bismuth on bacteria. In addition to bismuth, antimony and arsenic also exhibit modest antibacterial activity which necessitates the use of large doses. This is not always feasible due to their general toxicity and their lack of solubility in water.

Most prior art antibacterial agents suffered from significantly reduced utility when confronted with biofilm. "Biofilm" is a symbiotic community of bacteria (and sometimes other microbes including yeast) in which the entire community (which may also include different types of bacteria) acts, at least in part, as a single unit. Significant amounts of capsular polysaccharide is secreted and binds the organisms together. Metabolism and reproduction slow significantly relative to ordinary bacterial colonies. Biofilm is relatively unresponsive to most chemotactic intervention. The capsular polysaccharide prevents access of antibiotics to bacteria below the surface. Also, antibiotic mediated lysing of surface bacteria undesirably provide food for sub-surface bacteria. Antibiotics that function by attacking cell division and multiplication have little affect on biofilm bacteria which do very little dividing and multiplying.

SUMMARY OF THE INVENTION

It is an object of the present invention to provide more effective compositions and methods for broad antimicrobial applications, including prevention or inhibition of bacterial, fungal, or viral infection.

It is another object of the present invention to eradicate bacteria.

It is yet another object of the present invention to prevent spoilage.

It is yet another object of the present invention to provide methods and components for preventing the formation or growth of biofilm, and for reducing already-formed biofilm.

It is yet another object of the invention to treat psoriasis.

It is yet another object of the invention to treat thrush.

It is yet another object of the invention to treat Candida and Cryptococcal infections.

In one embodiment, the invention provides a method of suppressing bacterial growth comprising the step of supplying to a region for which said suppression is desired, an anti-bacterial agent comprising an antibacterial formulation selected from the group consisting of:

(A) a mixture comprising (i) a non-pyrithione complexing agent having at least one thiol group, and (ii) a group V metal or compound thereof said Group V metal being selected from the group consisting of bismuth, antimony and arsenic;

(B) a complex whose molecular structure includes (i) a non-pyrithione complexing agent having at least one thiol group, (ii) a Group V metal or compound thereof said Group V metal being selected from the group consisting of bismuth, arsenic and antimony; and (iii) a coordinate bond linking at least one sulfur atom of the thiol-containing complexing agent of subparagraph (B)(i) to the metal of subparagraph (B)(ii); and (C) a combination comprising the complex of paragraph (B) and at least one specie selected from the group consisting of (i) a thiol-containing complexing agent and (ii) a Group V metal or compound thereof, said Group V metal, being selected from the group consisting of bismuth antimony and arsenic.

The term "thiol" is used herein to refer to a compound that contains one or more sulfur atoms capable of existing in the form of sulfhydryl groups under appropriate pH conditions, e.g. significantly below the lowest pKa of the compound, regardless of whether such sulfur atoms are deprotonated or fully or partially protonated under conditions in which the thiol is used. "Thiol group" means a sulfur or an —SH group of a "thiol".

The terms "mixture" and "combination" encompass the use of two or more components in sufficiently close proximity to each other that they may interact with each other under conditions of end use for the antimicrobial agent of the invention, or for products which include said agent in accordance with the invention. Patients in need of treatment for a particular disease are those displaying symptoms or responding to diagnostic tests indicating presence of the disease in question. Patients in need of prophylactic intervention are those who through exposure or otherwise are at higher risk of contracting the disease in question than is the general population.

Antimicrobial agents described herein may be used to suppress microbial growth, reduce microbial infestation, treat products or surfaces to improve product resistance to microbial infestation, reduce biofilm, prevent conversion of bacteria to biofilm, prevent or inhibit microbial infection, prevent spoilage, and any other use described herein. It is also useful for a number of antiviral purposes, including prevention or inhibition of viral infection by herpes family viruses such as cytomegalovirus, herpes simplex virus Type 1, and herpes simplex virus Type 2. Other internal and external pharmaceutical uses of the microbial agents of the invention include, but are not limited to, treatment or prevention of bacterial infection, of tuberculosis, of *Helicobacter pylori* infection, and of peptic ulcer disease. In one embodiment, the agent is used at a dosage not generally lethal to bacteria but which is nonetheless sufficient to reduce protective polysaccharide coatings that would otherwise resist natural immune response. This technique is thus believed to aid immune system-mediated eradication of bacterial infection without harming human symbiotic microorganisms (e.g., normal intestinal flora and the like) to the extent that may be the case with antibiotics.

In one embodiment, the invention provides a method of reducing biofilm comprising the step of contacting biofilm with an antimicrobial agent comprising an antimicrobial formulation selected from the group consisting of:

(A) A mixture of (i) a pyrithione complexing agent, and (ii) a Group V metal or compound thereof, said Group V metal being selected from the group consisting of Bismuth, antimony and arsenic;

(B) a complex whose molecular structure includes (i) a pyrithione complexing agent, and (i) a Group V metal or compound thereof, said Group V metal being selected from the group consisting of bismuth, antimony and arsenic; and (iii) at least one coordinate bond linking said pyrithione complexing agent of subparagraph (B)(i) to the Group V metal of subparagraph (B)(ii); and (C) a combination of the complex of paragraph (B) and at least one species selected from the group consisting of (i) a pyrithione complexing agent and (ii) a Group V metal or compound thereof, said Group V metal being selected from the group consisting of bismuth, antimony and arsenic.

This same pyrithione-containing antimicrobial agent may be used to reduce biofilm by application of the agent to biofilm. It may also be used to suppress the conversion of bacteria to biofilm without eradicating the bacteria by contacting bacteria with a sub-lethal amount of the agent. Thus, this agent is suited to pharmaceutical uses that do not harm normal intestinal flora to the extent of more indiscriminate antibiotics. Other uses include limited treatment of thrush (e.g. with an otherwise ordinary mouthwash having 100 $\mu$M–1 mM antimicrobial agent; rinse 1–3 times daily). Other uses include, but are not limited to treatment of Psoriasis, other Candida infections, Cryptococci infections and others discussed herein.

In another embodiment, the invention provides a method of suppressing bacterial growth comprising the step of supplying to a region for which said suppression is desired at least one anti-microbial agent comprising an antimicrobial formulation selected from the group consisting of:

(A) a mixture comprising a di-thiol complexing agent and bismuth or a bismuth-containing compound;

(B) a complex whose molecular structure includes (i) a di-thiol complexing agent, (ii) bismuth or a bismuth-containing compound, and (iii) a coordinate bond linking at least one sulfur atom of the thiol-containing complexing agent to bismuth; and (C) a combination comprising the complex of paragraph (B) and at least one specie selected from the group consisting of (i) a di-thiol complexing agent and (ii) bismuth or a bismuth-containing compound;

wherein the molar ratio of bismuth to di-thiol complexing agent in said anti-microbial formulation is between 1:2 and 3:1;

wherein the di-thiol complexing agent of each of paragraphs (A), (B) and (C) has one thiol group bound to a first carbon atom and another thiol group bound to a second carbon atom, and wherein said first carbon atom is separated from said second carbon atom by 0–3 intervening atoms;

wherein a 5:10 mM solution of said group V metal:complexing agent has a light absorbance of at least 1.5 at a wavelength of 410 nanometers; and wherein at least 1% of said complex partitions from water into butanol when partitioning tests are run using equal volumes of water and butanol at 25° C. and a 5:10 mM solution of said metal to said complexing agent, respectively.

In another embodiment, the invention provides an antimicrobial agent comprising an antimicrobial formulation selected from the group consisting of:

(A) a mixture comprising (i) a complexing agent having at least one thiol group and no oxygen in its molecular structure, and (ii) a group V metal or compound thereof said Group V metal being selected from the group consisting of bismuth, antimony and arsenic;

(B) a complex whose molecular structure includes (i) a complexing agent having at least one thiol group and no oxygen in its molecular structure, (ii) a Group V metal or compound thereof said Group V metal being selected from the group consisting of bismuth, arsenic and antimony; and (iii) a coordinate bond linking at least one sulfur atom of the thiol-containing complexing agent of subparagraph (B) (i) to the metal of subparagraph (B)(ii); and (C) a combination comprising the complex of paragraph (B) and at least one specie selected from the group consisting of (i) a thiol-containing complexing agent with no oxygen in its molecular structure and (ii) a Group V metal or compound thereof, said Group V metal, being selected from the group consisting of bismuth antimony and arsenic, wherein said antimicrobial agent has at least one of the following characteristics:

(1) it is in a powder form;

(2) the antimicrobial formulation is in solution and the solution pH is below 7.0;

(3) the antimicrobial formulation is in an alcohol-containing solution;

(4) at least 1% of said complex partitions from water into butanol when partitioned using equal volumes of water and butanol at 25° C. and a 5:10 mM solution of said metal to said complexing agent, respectively; or (5) a 5 mM solution of said group V metal and a 10 mM solution of thiol-containing complexing agent has a light absorbance of at least 1.5 at a wavelength of 410 nanometers Other features and advantages of the present invention will become apparent from the following description of the invention which refers to the accompanying drawings.

DETAILED DESCRIPTION OF THE INVENTION

Figure 1:
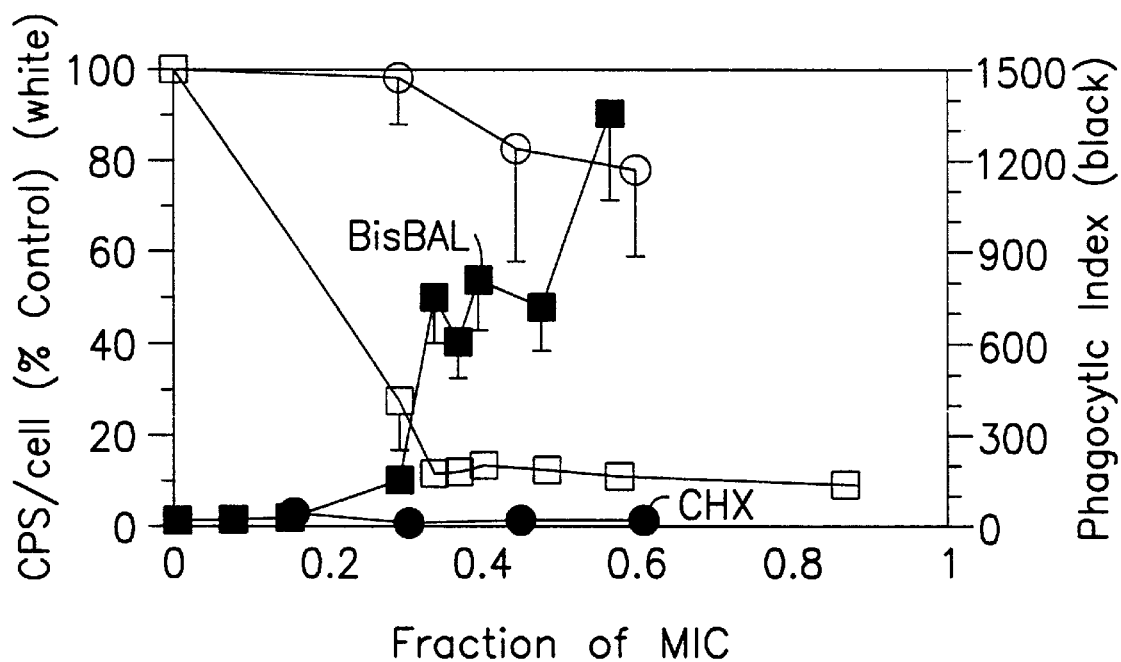
FIG. 1 is a graph showing the comparative effects on capsule and bacterial slime expression of bismuth:dimercaprol (BisBAL), a bismuth:dithiol complex according to the present invention, and chlorhexidine (CHX), a known topical agent useful as an antiseptic, a disinfectant and a preservative.

In accordance with the invention, a Group V metal and a thiol provide a synergistic level of activity, in excess of any modest activity that may be provided by either component individually. Without intending to be bound by theory, it is believed that in certain embodiments of the invention, the metal and thiol form a complex having a coordinate bond between the metal and at least one sulfur atom of the thiol. Formation of this complex may provide several different advantages. For example, the complex may have a more suitable solubility in both hydrophilic and lipophilic environments, and may thereby achieve better access to its target. Again without intending to be bound by theory, it is surmised that thiol may act as a carrier for the Group V metal and may deliver the metal to its target, thereafter becoming available to coordinate with, and provide similar transport and delivery for, another locally available metal. It is also hypothesized that bismuth may undergo thiol exchange between the carrier-thiol and thiols involved in biological processes. Addition of bismuth to thiol-containing enzymes likely has a detrimental effect on cellular and respiratory processes. In fact, the effectiveness of the metal:thiol complex is believed by the applicant to be at least partially due to reducing membrane potential in bacterial cell membranes which is directly responsible for producing energy. This concept was demonstrated when $E.$ $coli$ had a drop in membrane potential upon exposure to 5:2.5 $\mu$M solution of bismuth:2,3,-dimercaptopropanol.

Thus, the system of the invention tends to be in flux over time regarding the local concentration of (a) the complex, (b) uncomplexed thiol, and (c) uncomplexed metal. As explained in more detail below, the overall ratio of metal and thiol used in the antimicrobial agent of the invention may be varied over a wide range depending on the environment in which the agent will be used. The identity of the metal and the thiol may also vary with intended use and local environment. The form that the metal and thiol may take in accordance with the invention, and ways of facilitating complexing of one to the other, are discussed in more detail below in two separate sections, one section directed to the metal, and another section directed to the thiol.

It is particularly advantageous that in situ formation of the complex occurs easily in the presence of moisture. Microbial growth tends to be favored in a moist environment, and it is advantageous that the same environment which accelerates microbial growth also accelerates formation of a preferred complex for providing antimicrobial activity.

Because of the ability of the complex to form in situ, and because the synergy provided by mixing thiol and metal may not be entirely attributable to formation of the complex, the antimicrobial agent of the invention may be supplied in the form of a mere mixture of thiol and metal, or by placing thiol and metal in sufficient proximity that they may interact to provide anti-microbial activity. A "mixture" as used herein includes placing these components close enough to each other that they may interact against local bacteria or other targets, under conditions of use. Naturally, it is preferred that both the metal and the thiol be provided in a form that makes them easily accessible to each other, and facilitates coordinate bonding of one to the other to form the preferred complex.

Alternatively, the antimicrobial agent of the invention may be provided to its site of action in a form that already is primarily comprised of the metal:thiol complex, with only modest amounts of uncomplexed thiol or uncomplexed metal. This form of the invention may be manufactured in a number of ways. For example, metal and thiol may be dissolved in the same solution. Following formation of complex, the complex may be separated from uncomplexed thiol or uncomplexed metal by standard techniques including but not limited to precipitation of one component or the other, use of specific scavengers, adjusting pH, and other techniques to cause precipitation of the complex. In like manner, or by other known techniques, it is possible to remove any anion present in solution due to the metal having been originally supplied in the form of a metal salt. However, it is not strictly necessary to remove such an anion. The existence of such anions in the system, or even the incorporation of such anions into a crystal of a metal:thiol complex (if the complex is provided in powder or crystalline form) do not usually cause serious diminution of antimicrobial activity.

It is expected that both formation and degradation of complex may occur in situ, particularly when the agent of the invention is interacting with bacteria, or is otherwise in use. Thus, the relative concentration of complex, uncomplexed metal and uncomplexed thiol may change over time. It is, of course, possible to supplement one or more of these three ingredients either intermittently or continuously during use.

Either the metal, the thiol or the complex may be supplied in liquid or solid form. The antimicrobial agent of the invention may further include solvents, diluents, excipients, preservatives, emulsifiers, compounds for adjusting odor, taste, pH or the like.

It is not necessary to choose only a single metal or a single thiol for use in the antimicrobial agent of the invention. A plurality of different metals (e.g., bismuth and antimony together) may be used, as may a plurality of thiols (e.g., ethane dithiol and butane dithiol together). Metals and thiols are presented to the system in a variety of different manners. For example, one metal may be presented as a free ion while the other is added in the form of a salt. Even where only a single metal is used, some of it may be added freely and some may be added in salt form. A wide variety of different salts may be used. Likewise, one or more such variations are permitted when presenting the thiol component into the invention. These variations are interchangeable, although as discussed in more detail infra, certain preferences provide better results in certain contexts.

Not only may the antimicrobial agent of the invention be introduced to its site of operation in either liquid or solid form, but it is also possible to apply the agent in liquid form and evaporate away the solvent, leaving behind only dry components. For example, a catheter may be treated in accordance with the invention to prevent, for example, future bacterial growth during use. In one embodiment, the catheter may be dipped into a solution of the antimicrobial agent of the invention and then allowed to dry, leaving the dry components of the antimicrobial formulation of the invention on the catheter, where they remain during storage and until use. Other products may be dipped in like manner.

The Metals
The Presentation of the Metal

Several bismuth, antimony or arsenic salts can be used as the metal component of the invention. Although it is not required that metal be presented in salt form, metal salts are often used to put the metal in solution and make it available and accessible to the complexing agents of the invention which include thiol compounds. The preferred salts of the invention are the ones that make the metal more accessible and available to form a complex with the complexing agent. Examples of salts include, but are not limited to, metal nitrate, subgallate, citrate, oxide and subsalicylate. Preferably, the metal salt is a bismuth salt such as bismuth nitrate, colloidal bismuth subcitrate and bismuth subsalicylate. Bismuth has proven significantly more effective than antimony and arsenic in the antimicrobial agents of the invention. For example, in tests with dimercaprol as the thiol, bismuth outperformed antimony and arsenic by about one order of magnitude. Still both antimony and arsenic interacted with dimercaprol to produce better results than dimercaprol alone, arsenic alone or antimony alone.

Solubility of the Metal Salt

The activity of the metal:thiol complex can vary with the type of salt being used. One factor that can influence this activity is the solubility of the metal salt under conditions of use or of preparation of complex. One expected advantage for combining metal with complexing agent is the increased solubility of the metal. In addition, one presumes that the more soluble the metal salt is, the more of the metal will be available to complex with the thiol. In this regard, choosing the solvent in which the metal salt is dissolved can also have an effect on the activity based on solubility considerations for the metal salt.

Molar Ratio of the Metal:Complexing Agent

Another factor to consider in maximizing the solubility of the metal:complexing agent is its final molar ratio. This ratio is a factor in determining the final concentration of metal salt and thus can have an influence on the solubility of the metal salt. For instance, solubility of the metal salt is a more significant factor at high metal concentrations and at higher metal:complexing agent ratios.

The Influence of pH on the Selection of the Metal Salt

Yet another consideration in selecting the metal salt in order to maximize the metal:thiol complex activity is the desired pH of the metal:thiol complex solution being prepared, or the local pH where the invention is to be used, especially where complex is formed in situ. Preferably, the metal salt used has a good buffering capacity at a pH range that encompasses the desired pH of the final complex solution. This way, the salt can also be used as a buffer to maintain the pH of the complex solution within a certain limit. However, the metal salt does not have to act as a buffer in the complex solution particularly when such solution contains another salt that acts as the buffering agent.

It is important to note, however, that while the activity of the metal:thiol complex varies with the type of salt used, applicant determined that such activity is invariably significantly higher than the activity of the metal in the absence of thiol. Accordingly, the present invention encompasses the use of any metal salt that is fully or partially, or has the potential to be fully or partially, in solution with the complexing agent in the solvent where the invention will be prepared or used.

The Thiols
The Enhancement of Antibacterial Activity of Bismuth by Thiols and Pyrithione and Preferred Parameters of Enhanced Activity Applicant has determined that organic thiol compounds can enhance the antibacterial activity of bismuth. Some preferred thiols have one to two sulfhydryl groups, especially two. They are preferably amphipathic and can form coordinate bonds to bismuth, arsenic and antimony. Many are also alcohols, but the presence of a hydroxyl group does not appear to enhance activity. Indeed, some very active compounds, bismuth:propanedithiol and bismuth ethanedithiol contain no hydroxyl groups. However, the hydroxyl group seems to increase the stability of some Bis-thiols, such as bismuth:dimercaprol, without seriously hampering activity. The compounds bismuth:$\beta$-mercaptoethanol and bismuth:2-mercaptoethylamine are identical in structure except for the presence of a hydroxyl group with an amino group in bismuth:2-mercaptoethylamine at the same position. This difference amounted to a 5-fold decrease in bismuth:2-mercaptoethylamine activity and a different optimum molar ratio as compared with bismuth:$\beta$-mercaptoethanol. Though dimercapto-succinic acid is structurally similar to dimercaprol, the presence of acidic groups largely abolished synergy with bismuth. A oxygen atom (especially when not part of an alcohol group), an amine, and especially an acid group substitution on thiols diminished activity. Numerous other thiol compounds tested were not synergistic. with bismuth, suggesting that thiol groups without a carboxylate on a small hydrocarbon backbone (e.g. $C_6$ or less, especially $C_2$–$C_4$ is a preferred molecular configuration. Thiols having no atoms other than carbon sulfur and hydrogen have also proven particularly effective.

Applicant has discovered that dithiols are generally more active than monothiols, as they are better chelators. Lower levels of dithiols are required than of monothiols to achieve optimum activity. Approximately 3 times as much 3-mercapto-2-butanol as dimercaprol was required to achieve similar inhibitory activity. The compounds DMSA and dimercaptopropane-1-sulfonic acid are dithiols, and excellent bismuth chelators, but did not show antibacterial synergy, nor were they lipophilic. Lipophilicity of bismuth-thiol chelates is a very good predictor of antibacterial activity as discussed in more detail, infra. This model predicts that any hydrophobic monothiol, or any dithiol with at least a modicum of hydrophobicity will be synergistic with bismuth. Applicant also determined that compounds containing three or more thiols, such as trithiocyanuric acid and 2,5-dimercapto-1,3,4-thiadiazole, are also good chelators.

Accordingly, in a preferred embodiment, the present invention provides a composition comprising bismuth chelated by a thiol compound containing one sulfhydryl group such as a compound selected from the group consisting of 2-mercapto-3-butanol, β-mercaptoethanol, 2-mercaptoethylamine, and monothioglycerol.

Most preferably, the chelating compound contains a plurality of sulfhydryl groups (for example, two) such as a compound selected from the group consisting of 3,4-dimercaptotoluene, ethanedithiol, 2,3-butanedithiol, 2,3-dimercapto-1-propanol, 1,4-dimercapto-2,3-butanediol, 1,3-propanedithiol, and 1,4-butanedithiol. Thiols disclosed in the parent application hereto included dimercaprol, β-mercaptoethanol and dithiothreiotol. These three may be excluded, where desired, from any embodiment herein.

As a result of the variation in the levels of enhancement of activity of bismuth in the presence of different thiols, different models for predicting such enhancement are set forth below:

Vicinity of the Thiol Groups

The compound Bismuth-2,3-BDT (2,3-butanedithiol) appears to be as good as bismuth:ethanedithiol (discussed in more detail hereinafter) against most bacteria. However, Bismuth-1,4-butanedithiol (1,4-butanedithiol) had nearly 100-fold less activity, indicating that vicinal dithiols work much better than separated dithiols. Bismuth:propanedithiol (1,3-propanedithiol) works quite well, but not as well as the vicinal dithiols, suggesting that vicinal dithiols work best, followed by those separated by one carbon, while others are less effective.

Accordingly, in a preferred embodiment of the invention, each of two carbon atoms on the chelating thiol compound is linked to one sulfhydryl group, and the carbon atoms linked to the sulfur atoms are separated from each other by 0 to 3 intervening atoms, preferably 0 to 1 intervening atom. Most preferably 0, i.e., where these two carbon atoms are directly covalently linked.

Intensity of Yellow Color

Intensity of yellow color in aqueous solution is predictive of enhanced activity at high molar ratios of bismuth to thiol. Most bismuth-thiols show an absorbance at 410 nm with an absorption coefficient of 1.0 to 2.6, except for bismuth::dimercaprol and bismuth:propanedithiol, which had larger absorption coefficients (6.2 and 12.4, respectively). Bismuth:dimercaprol and bismuth:propanedithiol work optimally at high bismuth to thiol ratios (3:1 to 2:1). The yellow color is believed to arise from ligand to metal charge-transfer bands (LMCT), which are common to metal ion complexes. The combination of the "soft" $Bi^{3+}$ ion with the "soft" thiolate sulfur should favor ligand to metal charge-transfer bands. Therefore the intensity of yellow color can be used as a measure of the amount of bismuth-thiol complex formed and the extent of chelate formed. Yellow color in alkaline bismuth-thiol solutions can then be used to screen for thiols that best chelate bismuth at low concentrations. Accordingly, a 5:10 mM solution of the bismuth:dithiol composition of the present invention has a preferable light absorbance of at least 1.5, more preferably at least 10, at a wavelength of 410 nm.

Solubility in Butanol (Lipopholicity)

One expected advantage for combining bismuth with thiol is believed to be increased water solubility for the bismuth. Though lipophilicity of these agents is important for activity, water solubility is an obvious attribute. Solubility under a variety of conditions underscores the versatility and potential usefulness of bismuth-thiols. Many formulations and compositions are possible with these agents. Solubility in water is dependent on both pH and composition. For example, bismuth:dimercaprol is soluble in both acid or base, depending on the molar ratio. Also with bismuth:dimercaprol, a powder can be produced that retains most of the antibacterial activity. That bismuth:dimercaprol can be formulated to retain solubility in different environments, adds to the versatility of this class of compounds.

However, it is important to note that the most active bismuth-thiol in each of the bismuth-monothiol or bismuth-dithiol category is also the most soluble in butanol. Therefore solubility in butanol can predict what complexes of Bis-dithiols are maximally synergistic. Accordingly, in a preferred embodiment, a 5:10 mM solution of the bismuth-dithiol results in at least one percent, more preferably at least 10 percent and most preferably at least fifty percent, of a complex partitioning from water into butanol when partitioned using equal volumes of water and butanol at 25° C.

Influence of pH

The influence of pH on so many aspects of the chemistry of bismuth-thiols such as bismuth:dimercaprol is a reflection of the ionization of the thiol groups. With dimercaprol alone, the first thiol is fully deprotonated at pH 10, and the second at pH 11. This is dramatically altered when bismuth is added to the solution in a 1:2 molar ratio. Both deprotonations occur at much lower pH values, the first thiol complete at pH 5, and the second at pH 9. A reasonable conclusion is that the coordination of dimercaprol to the $Bi^{3+}$ ion promotes ionization. It can be assumed that dimercaprol remains coordinated to bismuth during this process. Without intending to be bound by theory, the change in solubility of bismuth::dimercaprol at pH 9 might be explained as follows. If the bismuth:dimercaprol complex is Bi(dimercaprol)$_2$, then when the two thiols are deprotonated, the complex should be more soluble, since it is more ionic. However, basic conditions promote the autoxidation of the thiols to disulfides, an event that is accelerated by the presence of bismuth. This explains why both instability and antibacterial activity increase from pH 4.5 to 9.0. All this activity can be enhanced further by increasing temperature and changing the molar ratio. With only one thiol ionized (pH 5–7), bismuth:dimercaprol exhibits less rapid activity. There is no activity and likely no complex formed below pH 4.5. Maximum activity and instability occurs at the optimum molar ratio at high pH and temperature. Thiols with low pKa's are preferred for use under significantly acidic conditions.

It is important to note that natural defenses for many microbes are significantly weakened at more acidic pH where they do not function as well. Normally, poisonous sulfhydryls and metals are removed by bacteria that use its own sulfhydryl compounds for protection (e.g., glutathione and DBS periplasmic enzymes). However, at pH 3 or less, these endogenous sulfhydryls are protonated and less active. For this reason, acid environment is preferred where possible. When in acid environment, thiols of the present invention that are active at more acidic pH (e.g. those with relatively low pKa's) are preferred. Such thiols advantageously deprotonate (in whole or in part) to better form the preferred thiol metal complex of the invention, while low pH simultaneously weakens the natural defenses of the target. A good example of this is 1,3-propanedithiol which is quite active in the presence of bismuth in a low pH environment. Accordingly, bismuth:propanedithiol can be used advantageously for the treatment of ulcers (e.g., weakening or eradication of *Helicobacter pylori*) in the acid environment of the stomach. In other embodiments, low pKa thiols of the invention may be supplied in an acidic medium in the first instance. While acidity is useful, it may also have an undesirable effect on formation of complex if pH is below the effective pKa of the chosen thiol in the presence of the metal. Thus, pKa is a very important criterion for selecting thiol where lower pH environments are expected.

Complexing the Metal with the Thiol

The chelation of bismuth, antimony and arsenic by thiol compounds in the form of a complex enhances their solubility and reduces the necessary dosage of these metals for effective treatment, thus decreasing any toxicity concerns. This chelation can be achieved, for example, by dissolving the thiol compound in a propylene glycol solution of bismuth, antimony or arsenic salt. Thereafter, samples can be further diluted to the desired concentrations using water or propylene glycol.

Bismuth-thiol Agents as Antiseptic Coatings

Implants or devices such as catheters, gastric tubes, endotracheal tubes, and prosthetic devices can be coated with bismuth-thiols to minimize adherence or persistence of bacteria, particularly staphylococci. Devices such as ventilators, water reservoirs, air-conditioning units, filters, paints, or other substances can be rendered biofilm-free for long periods. Small amounts of bismuth-thiols given orally or systemically after transplantation, bone replacement, during dental procedures, or during implantation may prevent colonization with staphylococci and other bacteria. Incorporating the agents into the device may be even more efficacious, providing slow release of antimicrobial agent locally for several weeks during healing.

Metal-pyrithione as Antibacterial, Antifungal and Antibiofilm Agent

Bismuth:pyrithione complex exhibits a significant increase in antibacterial activity over pyrithione alone or bismuth alone. Bismuth pyrithione also exhibits good antifungal activity against Candida and Cryptococcus.

Applicant has surprisingly discovered that bismuth:pyrithione complex is effective against biofilm, that it appears to penetrate bacterial slime, and reduce slime formation even in non-biofilm bacterial colonies. It is expected that antimony and arsenic will form similar complexes, although their effectiveness may lag that of bismuth as was the case with metal/thiol mixtures and complexes. Accordingly, the present invention provides a method of preventing the formation or growth of biofilms, or for reducing already formed biofilm by applying an effective amount of antimicrobial metal/pyrithione mixtures and complexes of the invention, wherein said metal is selected from the group consisting of bismuth, arsenic and antimony. Bismuth is preferred. The metal and pyrithione may be presented to the system in all of the different ways described above for metals and thiols.

Bismuth antibacterial activity can be enhanced up to 1000-fold in combination with certain thiol compounds. Bismith-thiols are active against a wide range of bacteria, and inhibit the expression of capsular polysaccharide (CPS). The thiol pyrithione (PYR) has excellent antibacterial and antifungal, activity, and also inhibits CPS expression. The combination of bismuth with PYR (BisPYR) exhibited superior properties. Bacteria inhibition was assessed by microbroth dilution in Mueller Hinton broth, according to NCCLS standards. Capsular polysaccharide expression was determined by growth in defined medium for 18 h, followed by cationic detergent extraction and alcohol precipitation of CPS, which was measured by uronic acid content. When combined at a 2:1 molar ratio, bismuth pyrithione (BisPYR) exhibited a 6-fold increase in antibacterial activity over PYR alone. The MBC (in PYR units) against several strains of vancomycin-resistant enterococci fell from 50–60 to 10–20 $\mu$M; against *Pseudomonas aeruginosa*, from 140 to 30 $\mu$M; and against *Staphylococcus aureus*, from 40 to 10 $\mu$M. Against *Klebsiella pneumoniae*, the MBC decreased 4-fold (60 to 15 $\mu$M), and CPS was inhibited by >90% at 2 $\mu$M. BisPYR was also tested against fungi by microbroth dilution in RPMI broth. Against several species of Candida and Cryptococcus, MICs for BisPYR were 2 to 10-fold lower than PYR alone. Aspergillis or Fusarium species were generally resistant to PYR and BisPYR. Compared to PYR, BisPYR was generally more active against a broad spectrum of bacteria and yeasts, and exhibited enhanced inhibition of CPS expression over that of bismuth or PYR alone.

The invention also provides for the pharmaceutical use of bismuth:pyrithione at dosages lower than generally required to be lethal to bacteria. It is anticipated that dosages for sub-lethal bismuth:pyrithione are about 50–150 $\mu$g bismuth per Kg body weight (administered intravenously). Orally, dosages would be 10–100 fold more, especially 1–10 mg per Kg body weight, especially 3–7 mg per Kg of body weight. Once or twice daily administration is recommended. Without intending to be bound by theory, it is believed that metal and pyrithione (mixture, complex, or both) will, when administered at sub-lethal dosages, reduce or eliminate the protective polysaccharide coat, thus leaving bacteria or yeast more susceptible to ordinary human immune response. This treatment has the advantage of substantially protecting normal healthy microbial colonies such as desirable intestinal flora and the like. It is likely that intravenous doses above 150 $\mu$g to about 1 mg would provide direct kill without significant toxicity to the patient.

Antiviral Properties of Bismuth:Thiols

Bismuth is not known to be an antiviral agent. In fact, neither $Bi(No_3)_3$ nor dimercaprol alone has any significant effect on the infectivity titer of several viruses. However, in vivo experiments indicated that the infectivity titers of cytomegalovirus, herpes simplex virus type 1 (HSV-1), and HSV-2 were significantly reduced after treatment with a bismuth:thiol composition in accordance with the invention. A mixture of 50 $\mu$M $Bi(No_3)_3$ and 25 $\mu$M dimercaprol (bismuth:dimercaprol) was utilized. Accordingly, the present invention provides a method of preventing or inhibiting viral infection caused by a virus selected from the group consisting of cytomegalovirus, herpes simplex virus type 1 and herpes simplex virus type 2, comprising the step of administering to a patient in need thereof, a therapeutically antiviral effective amount of a composition comprising a bismuth chelated by a thiol compound in the form a metal:thiol complex.

Molar Ratios of Bismuth-Thiol Combinations

Bismuth-thiol combinations were tested at a wide range of molar ratios to determine optimal activity. Though 4 to 6-fold less toxic when given intraperitoneally to mice than bismuth or dimercaprol alone, bismuth:dimercaprol is most toxic to mice at a 1:2 molar ratio. High thiol content also proved malodorous and irritating to the skin. Addition of bismuth nitrate to the thiol solution eliminated the sulfur odor and the irritating effects of dimercaprol at a 2:1 ratio, but not entirely at a 1:2 ratio. Bismuth-thiol compounds that achieve optimum activity only at higher thiol concentrations may have less utility, due to these unfavorable effects. The data indicate that each component of bismuth:dimercaprol mitigates the unfavorable characteristics of the other.

Accordingly, in a preferred embodiment of the invention, the molar ratio of the metal (preferably bismuth) to the thiol compound (preferably a dithiol) is from approximately 1:2 to approximately 3:1. More preferably, this molar ratio is from approximately 1:1 to approximately 3:1, still more preferably, from approximately 2:1 to approximately 3:1, and most preferably, approximately 3:1. As will be seen below, the preferences vary somewhat with the particular use to which the invention is being put.

Preferred Uses of the Invention

The invention is applicable to a wide variety of antimicrobial uses as described herein. The uses are as varied as surface disinfectants, topical pharmaceuticals, personal hygiene applications (e.g., antimicrobial soap, deodorant or the like), and systemic pharmaceutical products (e.g., for treating internal bacterial infection such as ulcers caused by *helicobacter pylori* ). Many other applications are discussed below. The invention may thus be incorporated into a wide variety of products. The invention may be used directly in any region already having microbial contamination, or may alternatively be used prophylactically in a region to suppress future contamination. A non-exclusive list of uses is set forth in column 1 of Table 1 below. Columns 2–4 set forth, for each use, set forth preferences regarding the manner in which certain parameters may be varied for best results. These preferences are in addition to those general preferences discussed elsewhere herein, and provide surprising benefits. For example, the lower molar ratio tends to enhance surface adsorbance of the invention components.

TABLE 1

| | Preferred Parameters | | |
|---|---|---|---|
| Applications | Thiol(s) | molar ratio of metal to thiol | solution pH |
| Coating of surfaces of medical devices | dimercaprol Ethanedithiol Pyrithione | 1:1–1:2 | 8–10 |
| Topical pharmaceutical | dimercaprol Ethanedithiol Pyrithione | 2:1 | 5–7 |

TABLE 1-continued

| | Preferred Parameters | | |
|---|---|---|---|
| Applications | Thiol(s) | molar ratio of metal to thiol | solution pH |
| Oral Pharmaceutical to treat ulcers caused by *helicobacter pylori* | 1,3-propanedithiol | 2:1 | ≦3 |
| Surface disinfectant | 1,3-propanedithiol | 2:1 | ≦3 |
| Deodorant | Ethanedithiol | 2:1 | 5–7 |
| Antimicrobial soap | Ethanedithiol | 2:1 | 6–8 especially 7 |

Pharmaceutical Use

As will be discussed below, metal:complexing agent can be administered to treat or prevent conditions in patients who are suffering or susceptible to suffer from a microbial infection. In particular, the compositions of the present invention are useful in treating or resisting acquisition of peptic ulcer disease caused by *helicobacter pylori*, herpes, psoriasis, candida infection, and cryptococcal infection. The recommended dosages for prophylactic use are the same as the therapeutic doses described herein.

In accordance with one aspect of the invention, once microbial (bacterial, viral or yeast) infection is determined, the metal:thiol complexing agent is administered at a dosage sufficient to reach and eradicate the microbe. It is however preferable to administer the antimicrobial agent of the invention at lower dosages (1–10 mg, preferably 5–10 mg of metal per Kg of body weight when administered orally, and 100 $\mu$g to 1 mg, preferably 500 $\mu$g to 1 mg of metal per Kg of body weight when administered intravenously) which are sufficient to weaken the bacterial coating making it more susceptible to natural human immune response. Naturally, the attending clinician may raise or lower dosage based on individual patient response.

When a metal: complexing agent (whether pyrithione or other thiol) is administered by the percutaneous or transmucosal technique, the delivered dosage may be raised or lowered in known ways, i.e., (1) by altering the location to which the lotion, ointment, cream, gel or patch is applied, (2) by altering the size of the surface area to which it is applied, (3) by altering the concentration of the active ingredient, (4) by altering the vehicle or carrier, or the like. For example, increasing the surface area will normally increase the dosage of active ingredient delivered if the concentration of active ingredient remains constant. In the same manner, dosage delivered increases with increased concentration of active ingredient in the delivery base, and decreases with decreased concentration. Changing the vehicle or carrier can also alter the delivered dosage in known ways. Subsequently, the patient may be monitored symptomatologically to verify that the symptomatic relief has been obtained, or by otherwise measuring infection by known techniques.

As used in the invention, a metal:complexing agent of the invention (whether pyrithione or other thiol) may be administered with or without additional carrier or diluent by the oral, systemic, percutaneous, transmucosal, or other typical route. In a pharmaceutical composition for oral administration, a metal:complexing agent is preferably present in a concentration between 5 and 99% by weight relative to total weight of the composition, more preferably between 50 and 99 percent, especially between 80 and 99 percent.

When prepared for percutaneous administration, a metal:complexing agent is preferably present in a concentration between 2 and 20% by weight relative to the total weight of the composition, more preferably between 5 and 15%, especially between 5 and 10%.

The metal:complexing agent can be administered by itself or in the presence of other antibacterial, antiviral or antifungal agents. In one embodiment, additional antifungal agents are added to metal thiol mixtures and/or complexes of the invention.

Oral Administration—Peptic Ulcer

For the treatment of peptic ulcer disease caused by *Helicobacter pylori*, the preferred mode of administration is oral and the preferred metal:complexing agent is a bismuth and 1,3-propanedithiol (at a 2:1 molar ratio, respectively) given at sub-lethal dosage of 100 $\mu$g–1 mg, preferably 500 $\mu$g–1 mg of bismuth per Kg of body weight. These dosages are expected to kill bacteria, especially at low pH. At least, it should suppress colonization and weaken bacteria for greater susceptibility to immune system response. Indeed, for that latter purpose, even lower dosages may be effective. The reasons the above dosages are expected to kill rather than merely weaken are (1) increased bacterial susceptibility at low pH and (2) the high potency of bismuth:1,3 proponedithiol under conditions of use. 1,3-propanedithiol is the preferred complexing agent for the treatment of *Helicobacter pylori* in the acidic environment of the stomach because of the low pKa's of its sulfhydryl groups. In acid environment, low pKa helps assure deprotonation of the thiol group, and thus more easy formation of desirable coordinate bonds between the metal and the thiol sulfurs.

When administered by the oral route, the antimicrobial agent of the invention may be formulated with conventional pharmaceutical excipients, e.g. spray dried lactose and magnesium stearate, into tablets or capsules for oral administration at concentrations providing easy dosage in a range from 100 $\mu$g to 1 mg, preferably, 500 $\mu$g to 1 mg per day per kg of body weight.

The active substance can be worked into tablets or dragee cores by being mixed with solid, pulverulent carrier substances, such as sodium citrate, calcium carbonate or dicalcium phosphate, and binders such as polyvinyl pyrrolidone, gelatin or cellulose derivatives, possibly by adding also lubricants such as magnesium stearate, sodium lauryl sulfate, "Carbowax" or polyethylene glycol. Of course, taste-improving substances can be added in the case of oral administration forms. The active substance can be also administered in solid dispersion state in appropriate carriers. Such carriers may, for example, be chosen from the group consisting of polyethylene glycols of molecular weight varying from 1,000 to 20,000 daltons and polyvinylpyrrolidone (e.g., Povidone from American Chemicals Ltd., Montréal, Canada).

As further forms, one can use plug capsules, e.g. of hard gelatin, as well as closed solf-gelatin capsules comprising a softener or plasticizer, e.g. glycerine. The plug capsules contain the active substance preferably in the form of granulate, e.g. in mixture with fillers, such as lactose, saccharose, mannitol, starches, such as potato starch or amylopectin, cellulose derivatives or highly dispersed silicic acids. In solf-gelatin capsules, the active substance is preferably dissolved or suspended in suitable liquids, such as vegetable oils or liquid polyethylene glycols.

Topical Administration—Psoriasis and Skin Infections

For the treatment of microbial skin infections or psoriasis, the preferred mode of administration is topical. Any pharmaceutically acceptable based typically used in the art for preparing topical gels, ointments, lotions, or the like may be used as the based. The antimicrobial agent of the invention is preferably provided at a concentration of 20$\mu$M–10 mM metal, more preferably 100 $\mu$M–1 mM. One to two applications per day to the affected area are recommended.

Transdermal Delivery

When the composition of the present invention is formulated as an ointment, lotion, gel, cream or the like, for transdermal administration, the active compound is admixed with a suitable carrier which is compatible with human skin or mucosa and which enhances transdermal or transmucosal penetration of the compound through the skin or mucosa. Suitable carriers are known in the art and include but are not limited to Klucel HF and Glaxal base which is available from Glaxal Canada Limited. Other suitable vehicles can be found in Koller and Buri, S.T.P. Pharma 3(2), 115–124, 1987. The carrier is preferably one in which the active ingredient(s) is(are) soluble at ambient temperature at the concentration of active ingredient that is used. The carrier should have sufficient viscosity to maintain the precursor on a localized area of skin or mucosa to which the composition has been applied, without running or evaporating for a time period sufficient to permit substantial penetration of the precursor through the localized area of skin. The carrier is typically a mixture of several components, e.g. pharmaceutically acceptable solvents and a thickening agent. A mixture of organic and inorganic solvents can aid hydrophilic and lipophilic solubility, e.g. water and an alcohol such as ethanol. Desirably, the carrier is one which, if formulated as 10% metal:complexing agent and 90% carrier (by weight) and applied twice daily in an amount providing 10 $\mu$g to 10 mg, preferably 100 $\mu$g to 1 mg, and more preferably 500 $\mu$g to 1 mg of metal in the form of metal:complexing agent to the afflicted area, will reduce or eliminate the infection or the symptoms of psoriasis.

The carrier may include various additives commonly used in ointments, lotions, gels, and creams and well known in the cosmetic and medical arts. For example, fragrances, antioxidants, perfumes, gelling agents, thickening agents such as carboxymethylcellulose, surfactants, stabilizers, emollients, coloring agents and other similar agents may be present.

The lotion, ointment, gel or cream should be thoroughly rubbed into the skin so that no excess is plainly visible, and the skin would not be washed in that region until most of the transdermal penetration has occurred, preferably, at least 15 minutes and, more preferably, at least 30 minutes after application.

A transdermal patch may be used to deliver the composition of the present invention in accordance with known techniques. It is typically applied for a long period, e.g. 0.5 to 4 days, but typically contacts active ingredients to a smaller surface area, allowing a slow and constant delivery of active ingredient.

A number of transdermal drug delivery systems that have been developed, and are in use, are suitable for delivering the active ingredient of the present invention. The rate of release is typically controlled by a matrix diffusion, or by passage of the active ingredient through a controlling membrane.

Mechanical aspects of transdermal devices are well known in the art, and are explained, for example, in U.S. Pat. Nos. 4,162,037, 5,154,922, 5,135,480, 4,666,441, 4,624, 665, 3,742,951, 3,797,444, 4,568,343, 4,064,654, 5,071,644, 5,071,657, the disclosures of which are incorporated herein by reference. Additional background is provided by European Patent 0279982 and British Patent Application 2185187.

The device may be any of the general types known in the art including adhesive matrix and reservoir-type transdermal delivery devices. The device may include drug-containing matrixes incorporating fibers which absorb the active ingredient and/or carrier. In a reservoir-type device, the reservoir may be defined by a polymer membrane impermeable to the carrier and to the active ingredient.

In a transdermal device, the device itself maintains active ingredient in contact with the desired localized skin surface. In such a device, the viscosity of the carrier for active ingredient is of less concern than with a cream or gel. A solvent system for a transdermal device may include, for example, oleic acid, linear alcohol lactate and dipropylene glycol, or other solvent systems known in the art. The active ingredient may be dissolved or suspended in the carrier.

For attachment to the skin, a transdermal patch may be mounted on a surgical adhesive tape having a hole punched in the middle. The adhesive is preferably covered by a release liner to protect it prior to use. Typical material suitable for release includes polyethylene and polyethylene-coated paper, and preferably silicone-coated for ease of removal. For applying the device, the release liner is simply peeled away and the adhesive attached to he patient's skin. In U.S. Pat. No. 4,135,480, the disclosure of which is incorporated by reference, Bannon et al. described an alternative device having a non-adhesive means for securing the device to the skin.

Intravenous Injection

Sterile solutions can also be administered intravenously. The active ingredient may be prepared at a final dose of 100 $\mu$g to 1 mg, preferably 500 $\mu$g to 1 mg per Kg of body weight of metal in the form of metal:complexing agent as a sterile solid composition which may be dissolved or suspended at the time of administration using sterile water, saline, or other appropriate sterile injectable medium. Carriers are intended to include necessary and inert binders, suspending agents, lubricants, flavorants, sweeteners, preservatives, dyes, and coatings.

Treatment in accordance with the invention is only desirable until all symptoms of the microbial infection are gone. One should be careful not prolong treatment for extended period of time beyond what is necessary so as to not compromise the existence of the flora in the body.

Addition of Antifungal Agents

If desired, the antimicrobial agents of the invention may be supplemented or intermixed with known antifungal agents, even if the agent of the invention itself has antifungal activity.

Bismuth:Dimercaprol as a Preferred Composition: Preparation, Molar Ratios, Dosages and Toxicity A bismuth-thiol composition, such as bismuth:dimercaprol, can be prepared by any standard method. In a preferred embodiment, in order to prepare a 1 ml solution of bismuth-thiol at 10 mM/5 mM (2:1 ratio), 200 $\mu$l of bismuth nitrate stock solution (48.5 mg $Bi(NO_3)_3$ in 10 ml propylene glycol) is added to 795 $\mu$l propylene glycol. Thereafter, 5 $\mu$l of a 1 Molar solution of thiol (in this case, 2,3-dimercaptopropanol) is added to the mix and shaken vigorously. In another embodiment, in order to prepare a 1 ml solution of bismuth-thiol at 10 mM/20 mM (1:2 ratio), 200 $\mu$l of bismuth nitrate stock solution (48.5 mg $Bi(NO_3)_3$ in 10 ml propylene glycol) is added to 778 $\mu$l propylene glycol. Thereafter, 20 $\mu$l of a 1 Molar solution of thiol (in this case, 2,3-dimercaptopropanol) is added to the mix and shaken vigorously. Sodium hydroxide is added to solubilize. The effect of subjecting bismuth:dimercaprol stock solutions to extreme temperatures on antibacterial activity were tested by heating to boiling and by autoclaving. Bismuth:dimercaprol was found to be resistant to boiling, but destroyed by autoclaving. Stability of various bismuth:dimercaprol preparations kept at room temperature and at 4° C. for long periods was tested periodically. Bismuth:dimercaprol was found to be a fairly stable compound. Bismuth:dimercaprol activity is stable for at least one month if kept at 4° C., but at room temperature (RT) a 500/600 $\mu$Mbismuth:dimercaprol solution will lose 50% of its activity in two weeks. A 500/150 $\mu$M bismuth:dimercaprol solution loses 50% of its activity at room temperature in a few days.

It has been found that the ideal molar ratio of bismuth to dimercaprol is in a ratio range of approximately 1:2 to 3:1. Bismuth:dimercaprol is most active against bacteria at 1:2, but the most stable form is at 2:1. Differing ratios can be used depending on the desired characteristics of the composition.

While it is not possible to bring 50 $\mu$M of $Bi^{3+}$ into solution in $H_2O$, 500 mM $Bi^{3+}$ goes into solution with 1.2 M dimercaprol present at pH 9–10. Furthermore since dimercaprol is lipophilic, bismuth:dimercaprol is soluble in acetone, ethanol, isopropanol, acetonitrile, DMSO, and even 1-butanol, but not in chloroform, octanol, ethyl acetate, or isoamylalcohol. However, different bismuth thiols have unique solubility profiles.

Based on gel filtration analysis, bismuth:dimercaprol at 2:1 ratio exists as a polycation. Bismuth:dimercaprol is highly positively charged on one end which adds to its water solubility in acid. On the other end, it is lipophilic and thus soluble in nonpolar solvents.

The affinity of dimercaprol for $Bi^{3+}$ is great since when the pH of concentrated bismuth:dimercaprol solutions drops below the alkaline range, a yellow precipitate forms. $Bi^{3+}$ alone forms a white precipitate. After sedimenting the precipitate, removing the supernatant and adding fresh alkaline buffer, the precipitate will redissolve and is active against bacteria, indicating that the precipitate is not $Bi^{3+}$ alone but rather intact bismuth:dimercaprol. This suggests that 1:2 bismuth:dimercaprol may precipitate in the acidic stomach, but will redissolve in the small intestine. Enteric-coated bismuth:dimercaprol would avoid such precipitation.

It has been found that the optimum $Bi^{3+}$ doses are in the range of 0.01 mg/kg to 357 mg/kg per day with the oral and topical dose not exceeding 500 mg/kg of dimercaprol and an injected dose not exceeding 50 mg/kg of dimercaprol. This is consistent with the extended regimen in humans for Pepto-Bismol@, in which 30 ml (525 mg Bismuth subsalicylate) are administered four times a day (2.1 g/day) for 3 weeks. Maximal intake of Bismuth subsalicylate in humans is 4.2 g/day. This is the equivalent of 18 mg/day of $Bi^{3+}$ in a 30 g mouse, or 600 mg/kg/day, or 300 mg/kg bid. The maximum oral dose of $Bi^{3+}$ in Bismuth subsalicylate for humans is similar to the highest safe dose of bismuth:dimercaprol for mice. Thus, the maximum $Bi^{3+}$ concentration already established for other therapeutic $Bi^{3+}$ compounds need not be altered for bismuth:dimercaprol therapy. Surprisingly, bismuth:dimercaprol is less toxic than existing $Bi^{3+}$ compounds, even though it is up to 1000-fold more potent against bacteria. It has been found that dimercaprol is the limiting factor, since at high doses dimercaprol is toxic, with rapid death accompanied by severe tremors.

When injected intraperitoneally into mice, bismuth:dimercaprol ($LD_{50}=140\pm40mgBi^{3+}$/kg) was considerably less toxic than $Bi(No_3)_3$ ($LD_{50}=52\pm13mgBi^{3+}$/kg) or Bi-cysteine ($LD_{50}=49\pm12mgBi^{3+}$/kg), based on two separate trials. Mice can tolerate 60 mg $Bi^{3+}$/kg in the form of bismuth:dimercaprol intraperitoneally without signs of morbidity or mortality for at least 5 days. Therefore $Bi^{3+}$/kg is less toxic as the bismuth:dimercaprol chelate than in other compounds, especially when given intraperitoneally.

Bismuth:dimercaprol is active against a broad range of bacteria. It is particularly effective against *H. pylori, S. aureus* and *C. difficile*, and is least effective against the enterococci and certain anaerobes. Of 47 methicillin-resistant *S. aureus* tested, none showed any indication of resistance. Most bacteria are inhibited by bismuth:dimercaprol below 17 μM $Bi^{3+}$. However, in agar dilution studies, the MIC was 3-fold higher for *E. coli*, suggesting neutralization of bismuth:dimercaprol activity by components in the agar medium. The data from agar diffusion studies correlate well with that seen in broth culture.

Bismuth-Ethanedithiol (BisEDT)

A preferred Bis-thiol composition for many applications is bismuth:ethanedithiol. It is a stronger antimicrobial agent than bismuth:dimercaprol. It is typically 4-fold better against most bacteria and 10-fold better against very resistant organisms, such as Burkholderia or vancomycin-resistant enterococci. The greatest improvement is against *Staphylococcus epidermidis*, a normal skin bacteria, yet an opportunistic pathogen that slimes up implants, such as artificial hips, heart valves, catheters. The MIC or bismuth:ethanedithiol needed to inhibit *S. epidermidis* ATCC 12228 was 0.1 μM $Bi^{3+}$, which is less bismuth than is normally found in soil. Ten methicillin-resistant *S. epidermidis* (MRSE) were all sensitive between 0.85 and 1.75 μM bismuth in bismuth:ethanedithiol. Extremely low concentrations of bismuth:ethanedithiol (6 μM bismuth) can inhibit all bacteria, including anaerobes, gram-positive and gram-negative bacteria, and antibiotic-resistant bacteria. That is a 1000-fold better than other nonthiol bismuth compounds.

Here are the species of bacteria sensitive to bismuth:ethanedithiol thus far: *Burkholderia cepacia, Enterococcus faecalis*, Stenotrophomonas spp., *Serratia marcescens, Proteus vulgaris, Enterobacter cloacae, Salmonella enteritidis, Escherichia coli, Klebsiella pneumoniae, Pseudomonas aeruginosa, Staphylococcus epidermidis, Staphylococcus aureus, Providencia, stuartii, Listeria monocytogenes, Mycobacterium tuberculosis, Vibrio cholerae, Aeromonias hydrophila,* Legionella spp., Group B Streptococci, *Streptococcus pyogenes, Streptococcus pneumoniae, Haemophilus influenzae, Shigella flexner, Helicobacter pylori, Mycobacterium avium, yersinid enterocolitica,* and *campylobacter* spp. Anaerobes tested were also all sensitive between 1 and 8 μM $Bi^{3+}$, including 6 strains of *Clostridium difficile*, 2 strains of *Clostridium perfringens*, and 2 of *Bacteroides fragilis*.

One of the disadvantages of using ethanedithiol is its foul odor. However, when bismuth and ethanedithiol are combined, it no longer smells. Most every other aspect of bismuth:ethandithiol is advantageous. Compared to bismuth:dimercaprol, bismuth:ethanedithiol is 50 times cheaper, and no more toxic. bismuth:ethanedithiol lethality to mice is very similar to that of dimercaprol, according to accompanying MSDS sheets from Aldrich Chemical Company. Bismuth:ethanedithiol is less toxic than bismuth:dimercaprol simply because less is needed. It is also a more stable compound at all molar ratios and pHs.

Experimental Details

Bacterial Strains and Cultivation

Bactrol reference cultures (Difco Laboratories, Detroit, Mich.) were used to test a broad spectrum of bacteria. Bactrol strains include *Enterobacter cloacae* ATCC 23355, *E. coli* ATCC 25922, *Klebsiella pneumoniae* ATCC 13883, *Proteus vulgaris* ATCC 13315, *Pseudomonas aeruginosa* ATCC 27853, *Serratia marcescens* ATCC 8100, *Staphylococcus aureus* ATCC 25923, *Streptococcus pyogenes* ATCC 19615, *Enterococcus faecalis* ATCC 29212 and *Salmonella typhimurium* ATCC 14028. Other enteric pathogens used were enterotoxigenic *E. coli* ATCC 43896, enterohemorrhagic (verotoxin-producing) *E. coli* ATCC 35150, *Shigella flexneri* ATCC 12022, and *Yersinia enterocolitica* ATCC 27729. Vancomycin-resistant enterococci (VRE) and methicillin-resistant *S. aureus* (MRSA) were clinical strains. *Legionella pneumophila* strains 3–69, B2-5-D1, ATCC 33152, and the Glover isolate were provided by Binax, Inc. Anaerobic bacteria included *Clostridium difficile* ATCC 9698, *Bacteroides fragilis* ATCC 23745, and one *Bacteroides fragilis* clinical isolate, *Clostridium histolyticum* ATCC 19401, *Clostridium perfringens* ATCC 13124, *Bacteroides ovatus* ATCC 8483, and *Actinomyces odontolyticus* ATCC 17929. Another strain tested was *E. faecium* ATCC 2358. Anaerobic culture conditions were established by using the BBL GasPak Plus system. Anaerobic bacteria were cultured on Trypticase Soy Agar containing 5% sheep blood (BBL, Cockysville, Md.), six antibiotic-resistant *H. pylori* clinical strains were cultured on Mueller-Hinton blood agar in BBL Campy Pouch Microaerophilic Systems (Becton Dickinson, Cockeysville, Md.).

Susceptibility Studies

Susceptibility studies were performed by several methods, including broth dilution, agar dilution, and agar diffusion. For broth dilution studies, starter cultures were grown to mid-log phase at 35° C. for 4 h at 200 rpm, were used to prepare 0.5 McFarland standard suspensions, which were further diluted 1:100 ($5\times10^5$ CFU/ml) in Mueller-Hinton broth medium (BBL). Cultures were incubated and monitored for turbidity in an Avantage Microbiology System (Abbott Laboratories, Irving, Tex.). Growth inhibition was determined by monitoring lag times before initiation of culture growth (6), and by standard plating of bacteria in triplicate at 24 h growth. Culture lag times were obtained from computer-generated growth curves. The MIC was expressed as the lowest drug concentration that inhibited turbidity for 24±2 h. Viable bacterial counts (CFU/ml) and subcultures were performed by standard plating on Nutrient Agar (BBL). For agar diffusion studies, a sterile swab was used to spread a 0.5 MacFarland standard onto Nutrient Agar. Absorbent paper disks were placed on the agar surface. Disks were impregnated with up to 15 μl of solutions containing bismuth nitrate, dimercaprol, or both.

Plates were incubated overnight at 36° C. The diameter of the zone of inhibition, including the 6 mm disk diameter was measured with vernier caliper. Agar diffusion studies were generally performed on Mueller-Hinton II agar. Legionella strains were cultured and tested on BCYE agar (BBL). For agar dilution studies ( *H. pylori* and anaerobes), Mueller-Hinton blood agar was prepared containing bismuth:dimercaprol. Molten Mueller-Hinton agar medium was cooled to 50° C., and def ibrinated horse blood was added to a final concentration of 5%. Bismuth:dimercaprol powder was added progressively while pouring agar plates, producing agar medium with incremental concentrations of bismuth:dimercaprol. Suspensions equivalent to a No. 1 MacFarland standard of *H. pylori* were spotted (10 μl) on the agar surface. Plates were incubated in Campy pouches at 370° C. for five days. The MIC was expressed as the lowest drug concentration that inhibited growth.

Bactericidal assays were performed in broth medium. Minimal bactericidal concentrations were recorded as the concentration of drug that reduced the initial viable bacterial count by 99.9% at 18–24 h incubation. Viable bacterial counts were determined by standard plating on appropriate agar media. The influence of pH on bactericidal activity was determined by washing log phase *E. coli* ATCC 25922 cells in saline and adjusting the viable count to $10^9$ CFU/ml. Samples were prepared containing 10 mM of the following buffers at the indicated pH: citrate, pH 4; 2 [N-morpholino]ethanesulfonic acid (MES), pH 5 and pH 6; 3[N-morpholino]propanesulfonic acid (MOPS), pH 7; Tris [hydroxymethyl]aminomethane (TRIS), pH 8 and pH 9. Phosphate buffers (10mM) at pH 3 and pH 4 were also used. Bismuth:dimercaprol was added to samples at 100 µM. Cultures were incubated at 36° C. for 24 h and sampled repeatedly for colony count.

Bactericidal activity of bismuth:dimercaprol against *E. coli* ATCC 25922 was assessed at several temperatures. A saline suspension of $10^9$/ml late-log phase bacteria was incubated with 75/37.5 µM bismuth:dimercaprol at 25° C., 35° C., 42° C., and 50° C. Bacterial viability was determined by standard agar plating on Nutrient Agar (BBL).

Stability and Solubility

Bismuth:dimercaprol (BisBAL) was prepared at molar ratios between 2:1 and 1:2 by adding 2.5 to 10 µl 10M dimercaprol (Sigma Chemical Co., St. Louis, Mo.) to 1 ml of 50 mM Bi(No$_3$)$_3$ in propylene glycol. Samples were diluted in water or propylene glycol. The final concentration of propylene glycol was kept ≦1% to avoid confounding antibacterial effects. The pH was adjusted by addition of 10N NaOH or concentrated HC1. Samples were tested weekly for stability against *E. coli* ATCC 25922 in broth cultures. Solubility testing involved mixing bismuth:dimercaprol components at various molar ratios, and sedimenting precipitates by centrifuging for 2 min in an Eppendorf 5415 Microfuge. Sedimented bismuth:dimercaprol was lyophilized in pre-weighed tubes. Sediment weight was measured and divided by 20.8 (total weight in mg of components) to obtain percent solubility. Titration experiments involved addition of NaOH to 5 ml of 100 mM dimercaprol or 50/100 mM BisBAl in water and recording the pH increment after each addition of hydroxide.

The lipophilicity of bismuth-thiols was assessed by two-phase separation in 1-butanol. Bismuth-thiol solutions were prepared at 5/10 mM in purified water at pH 9–10 by addition of 10 N NaOH. An equal volume of 1-butanol was added, the tube mixed vigorously for 30 sec, and pulse-centrifuged to separate liquid phases. Absorbance ($A_{410 nM}$) of the bright yellow solution was recorded in both phases in a Milton Roy Spectronic 601 UV/VIS spectrophotometer at a wavelength of 410 nm. The Absorbance of bismuth:dimercaprol was greater in butanol than in water, and was adjusted to 0.8 of the raw absorbance data.

Biochemicals

Stock solutions of 50 mM Bi(NO$_3$)$_3$ (Sigma) were prepared in propylene glycol (Sigma). Thiol reagents and complexing agents obtained from Sigma were added at various ratios. The standard molar ratio in screening for synergy was 1:2 bismuth to thiol. All solutions were prepared daily and kept at room temperature, except those used in stability studies.

EXAMPLE 1

Toxicity of Bismuth:Dimercaprol

Experiments of the toxicity of bismuth:dimercaprol were performed in 35 g Swiss-Webster female mice. Bismuth:dimercaprol was administered orally and intraperitoneally. As shown in Table 2, mice tolerated 12.5 mg of Bi$^{3+}$ orally (357 mg/kg; 50 equivalent human doses) with fairly high doses of dimercaprol. Combined with Bi$^{3+}$, dimercaprol doses of 500 mg/kg were innocuous, while 1 g/kg killed all of the mice within a few hours. When given alone, dimercaprol at 500 mg/kg killed all of the mice within an hour, and dimercaprol at 250 mg/kg killed one of five mice.

The oral LD$_{50}$ for dimercaprol alone is calculated to be 333 mg/kg. The intramuscular LD50 for dimercaprol alone in rats is 86.7 mg/kg (Merck Manual). The intraperitoneal LD$_{50}$ for dimercaprol in mice is 60 mg/kg. The oral LD$_{50}$ for mice is over 5-fold higher, presumably due to limited absorption of dimercaprol from the gut. The oral LD$_{50}$ for dimercaprol in bismuth:dimercaprol is even higher at 556 mg/kg. Evidently, Bi$^{3+}$ lessens oral toxicity of dimercaprol. Thus, dimercaprol is the toxic moiety in bismuth:dimercaprol oral preparations, but is not as toxic orally when combined with Bi$^{3+}$. Indeed, dimercaprol given orally in bismuth:dimercaprol is nearly 10 times less toxic than is dimercaprol given intraperitoneally.

The threshold toxic intramuscular dose for dimercaprol in humans is less than 5 mg/kg (Sulzberger, 1946), which is one-hundredth the dimercaprol that was tolerated orally as bismuth:dimercaprol. These data suggest that dimercaprol toxicity should not be problematic during bismuth:dimercaprol therapy since the minimal inhibitory concentration (MIC) for dimercaprol in bismuth:dimercaprol is 100–500 µg/kg.

TABLE 2

| Agent | Oral LD$_{50}$ (mg/kg) | IP LD$_{50}$ (mg/kg) |
|---|---|---|
| Bi (NO$_3$)$_3$ | >357 | 53 ± 13 |
| BAL | 333 ± 60 | 60 ± 10 |
| BisBAL | 357/556 ± 25 | 142 ± 54/234 ± 91 |
| Bi-cysteine | 156 ± 20 | 49 ± 12 |

In additional experiments, burned mice were challenged with *K. pneumoniae* to investigate the topical toxicity of bismuth:dimercaprol. When bismuth:dimercaprol at 376/621 mg/kg was applied topically or subeschar mortality was hastened by 2–3 days. However, 38/62 mg/kg did not hasten mortality when applied topically and 3.8/6.2 mg/kg did not affect mortality when applied either topically or subeschar. The lethality of bismuth:dimercaprol in a burn wound sepsis model paralleled that seen in oral models. The data indicates that the threshold for dimercaprol toxicity, orally or topically, in the form of bismuth:dimercaprol is greater than 500 mg/kg, while the systemic toxicity threshold is greater than 50 mg/kg.

As a disinfectant, or for use on inanimate surfaces, bismuth:dimercaprol concentrations can exceed the limits set forth above. In particular, concentrations up to and exceeding 500 mM Bi$^{3+}$ and 1M dimercaprol can be used for disinfectant purposes. Further, concentrations as low or lower than 50 µM Bi$^{3+}$ and 100 µM dimercaprol can be used for antiseptics or preservatives.

Another consideration is the toxicity of bismuth:dimercaprol for mammalian cells. Bismuth:dimercaprol was not notably cytotoxic or pro-inflammatory based on animal studies and other informal observations. There was no evidence of blood or mucus in the stools of treated animals, nor any signs of irritability from massive doses of bismuth:dimercaprol. Accidental contact on hands with small amounts of dimercaprol can be quite irritating, whereas bismuth:dimercaprol is not irritating to the skin even at 100-fold the dimercaprol concentration. Dimercaprol alone is very toxic and extremely irritating to gastric mucosa when applied as 5% solutions (Cattell, 1942). Preliminary results further showed that bismuth:dimercaprol was not cytotoxic to neutrophils, even at 100× bacteriostatic concentrations.

EXAMPLE 2
Antimicrobial Activity of Bismuth:Dimercaprol Bacteria and Culture Conditions Nosocomial pathogens were employed to determine the range of bismuth:dimercaprol antimicrobial activity. The following bacteria were cultured in a standard broth medium, e.g., Mueller-Hinton II, overnight: *Klebsiella pneumonia* O1:K2 strain 52145, Non O1 *Vibrio cholerae* strain NRT36S, *Salmonella enteritidis* strain ATCC 14028, *Shigella flexneri* ATCC 12022, *Yersinia enterocolitica* ATCC 27729, enterohemorrhagic *Escherichia coli* 0157:H7 (ATCC 35150), and enterotoxigenic *Escherichia coli* ATCC 43896. Anaerobes included *Clostridium perfringens* ATCC 13124 and *Bacteroides fragilis* ATCC 23745. Ten *Pseudomonas aeruginosa* strains resistant to aminoglycoside antibiotics were obtained from the Schering-Plough collection. Several clinical isolates of Providencia, Serratia, and Xanthomonas were tested; Proteus strains included *P. vulgaris* O:19, *P. vulgaris* ATCC 49990, *P. mirabilis* ATCC 49995, *P. mirabilis* ATCC 51286, and *P. mirabilis* ATCC 49565, *Pseudomonas cepacia* Isolates of *H. pylori*, methicillin-resistant *S. aureus* (MRSA) and vanomycin-resistant enterococci (VRE) were also used. Reference strains of *Staphylococcus aureus* (ATCC 25923), *Excherichia coli* (ATCC 25922), and *Pseudomonas aeruginosa* PAO1 were provided for comparison. Pyoverdene mutants of *P. aeruginosa*, PAO6609 and K394 were employed. The following iron receptor mutants were used: *E. coli* H1443 (wt), *E. coli* H854 (fiu), *E. coli* C1087 (cir), *E. coli* C1072 (tonB), *E. coli* AB1515-and *E. coli* AB1515-1F ($Fe^{2+}$ transport deficient). Multiple antibiotic resistance (mar) and sox mutants of *E. coli* were utilized and included strains MC4100 (wt), MC4100/p9 (Mar), MC4100 Tn9 Δ1738 and MC4100 Tn1Okan soxR201. These strains were maintained by subculture on agar medium containing ampicillin (50 μg/ml), kanamycin (20 Mg/ml), or chloramphenicol (10 μg/ml) as needed. *Vibrio cholerae* strains included 395, 569, El tor Ogawa N16961, El tor Inaba P27459, 1837, 168019, and MO-10. Strains 1837, 168019 and MO-10 are known to have capsules. Bacteria were subcultured weekly on Blood or Nutrient agar plates.

A Mueller Hinton II broth (BBL Systems, USA) was the culture medium used in most susceptibility studies. A chemically-defined medium with excess glucose and limiting nitrogen (DW) was used to promote capsule production in *K. pneumoniae* cultures (Domenico, 1991). MacFarland standard suspensions (0.5) were prepared from mid-log phase starter cultures and further diluted 1:100 into test medium. Bacteria were placed in customized research cuvettes with chemotherapeutic agent, and loaded in the Advantage System (Abbott Laboratories, USA). Cultures were rocked slowly at 34.5° C. and monitored repeatedly at A670 nm. Inhibition was assessed by recording lag times before initiation of culture growth. Lag times were obtained from computer-generated growth curves. The 24 hour inhibitory concentration ($IC_{24}$) was defined as the average antibiotic concentration (N≧3) that produced a culture lag time of 24±1 h. This data provided parametric parameters for statistical measurement (i.e., Student's t test). Some bacteria were analyzed for susceptibility by agar diffusion on blood or Mueller-Hinton agar plates, with adherence to NCCLS standards. Bactericidal activity (99.9% reduction in CFU/ml) of various mixtures of bismuth:dimercaprol was evaluated in liquid medium using *E. coli* ATCC25922. *H. pylori* susceptibility to bismuth:dimercaprol was tested on blood agar plates in Campy pouch bags (Becton Dickinson, Cockeysville, Md.) on Blood agar. Plates were incubated at 36° C. for 5 days. Susceptibility was also measured by agar dilution.

The culture medium component effects on bismuth:dimercaprol activity were assessed in chemically-defined medium by adding limiting or excessive amounts of each essential ingredient. Oxygen tension effects were determined by agar diffusion in aerobic, microaerophilic (Candle jar), and anaerobic (GasPak) conditions. Filter paper discs were impregnated with 157 μg $Bi^{3+}$, 186 μg dimercaprol or 157 μg/31 μg bismuth:dimercaprol (3:1 molar ratio). Other amounts and ratios were tested. Culture condition effects, such as pH or temperature were evaluated in broth mediums.

Resistant Bacteria

Aminoglycoside-resistant *Pseudomonas aeruginosa* strains were tested, including both enzyme-inactivating and reduced permeability strains. Multiply-resistant (mar or sox) mutants of *E. coli* were tested, since such bacteria use afflux mechanisms to resist antibiotics. Several clinical isolates of Providencia, Serratia and Xanthomonas were examined for bismuth:dimercaprol sensitivity, since these bacteria tend to be resistant to chlorhexidine (CHX). Proteus also tends toward resistance to chlorhexidine. Pseudomonas cepacia was tested. This is one of the most resistant species.

Results

Bismuth:dimercaprol was found to be particularly effective against gram-positive organisms such as methicillin-resistant *Staphylococcus aureus* (MRSA). Even vancomycin-resistant enterococci (VRE) were inhibited by bismuth:dimercaprol. Zone diameters of inhibition produced by agents against both antibiotic-resistant species after 24 h incubation at 37° C. are summarized in Table 3.

TABLE 3

Susceptibility of resistant Gram-positive bacteria to bismuth:dimercaprol

| Bacterial | Zones of Inhibition (mm) for: | | |
|---|---|---|---|
| Strain (# of isolates) | $Bi(NO_3)_3$ (157 μg) | BAL (186 μg) | BisBAL (157/31 μg) |
| MRSA (27) | 7.3 ± 2.8 | ≦6.0 | 18.6 ± 3.5 |
| VRE (10) | 7.3 ± 1.4 | ≦6.0 | 9.7 ± 0.8 |

All strains of vancomycin-resistant enterococci and methicillin-resistant *S. aureus* tested were inhibited by bismuth:dimercaprol, but were minimally inhibited by $Bi(NO_3)_3$ and not inhibited by dimercaprol alone. methicillin-resistant *S. aureus* were particularly sensitive, showing a further partial zone of inhibition of 27.9±2.5 mm. No partial zones were seen with vancomycin-resistant enterococci isolates.

Gram-negative bacteria were also found to be quite sensitive to bismuth:dimercaprol. All of the gut pathogens were uniformly sensitive. Using the 24 hour inhibitory concentration ($IC_{24}$) as the endpoint, the following bacteria were grown in Mueller-Hinton II overnight: *Vibrio cholerae, Salmonella typhimurium, Shigella flexneri, Yersinia enterocolitica*, enterotoxigenic and enteroinvasive *E. coli. E. coli* and Salmonella grew well in the presence of 250–500 μM $Bi^{3+}$, while *V. cholerae, S. flexneri*, and *Y. enterocolitica* could withstand up to 50 μM $Bi^{3+}$. Neither the culture lag time nor the final culture turbidity at 18 hour was affected more than marginally by these $Bi^{3+}$ concentrations. In stark contrast, $Bi^{3+}$ at 12 μM(4.3 μg/ml) combined with 3 μM dimercaprol (0.37 μg/ml) was completely inhibitory to all bacteria. Bacteriostatic and bactericidal concentrations for *E. coli* ATCC 25922 were similar (approx. 15 μM $Bi^{3+}$/5 μM dimercaprol). Multiply-resistant (mar or sox) mutants of *E. coli* were also equally sensitive to bismuth:dimercaprol.

Other gram-negative aerobic bacilli, such as *K. pneumoniae* ($IC_{24}$=30/10 µM) and *Pseudomonas aeroginosa* ($IC_{24}$=8/2.7 µM) also showed sensitivity to bismuth:dimercaprol. Of the 10 *P. aeruginosa* strains resistant to aminoglycoside antibiotics, all were equally sensitive to bismuth:dimercaprol, regardless of whether they were aminoglycoside permeability or enzyme-inactivating mutants. Six strains of Proteus, two of Providencia and one Serratia strain also showed low sensitivity (≦30/10 µM). Seven Xanthomonas isolates were similarly sensitive. Seven strains of *V. cholerae* including Ogawa and Inaba, were all sensitive below 15/5 µM bismuth:dimercaprol. A single clinical isolate of *Burtcholderia cepacia* was the only strain showing higher MICs (90/30 µM).

Anaerobes were also tested, with *Actimomyces odontolyticus* being inhibited at 22.5/45 µM, Clostridium spp. at 50/100 µM, and Bacteroides spp. at 100/200 4M bismuth:dimercaprol. *Helicobacter pylori* shows sensitivity to bismuth:dimercaprol between 1 and 6 µM $Bi^{3+}$.

As the data clearly shows, all of the gram-positive and gram-negative bacteria and anaerobic and aerobic bacteria tested were sensitive to bismuth:dimercaprol. It should be noted that the greater resistance against bismuth:dimercaprol which was found among Bacteroides may be useful, since they are considered normal flora in the gut. In addition, bismuth:dimercaprol has been found to be particularly active against both staphylococci and *P. aeruginosa*, which is an unusual and very useful characteristic for an antibacterial agent.

Since bacteria inhabiting the gastrointestinal tract thrive under anaerobic conditions, the inhibitory potency of bismuth:dimercaprol in an anaerobic environment was determined. Six *E. coli* were tested by agar diffusion, using a BBL GasPakPlus Anaerobic system (Becton Dickinson, Cockeysville, Md.). The strains chosen were those which had been used in iron uptake studies, since bismuth antibacterial activity can be reversed by iron. The results are summarized in Table 4.

TABLE 4

Influence of Anaerobic Conditions on Bi/BAL Sensitivity

| Bacteria | Zone diameter (mm) for BisBAL: | |
|---|---|---|
| | $+O_2$ | $-O_2$ |
| *E. Coli* AB1515-1 (wt) | 12.6 | 11.0 |
| *E. coli* AB1515-1F ($Fe^{2+}$) | 15.0 | 11.8 |
| *E. coli* H1443 (wt) | 11.8 | 10.0 |
| *E. coli* H854 (fiu) | 11.4 | 10.0 |
| *E. coli* C1087 (cir) | 11.9 | 11.4 |
| *E. coli* C1072 (tonB) | 12.2 | 10.4 |

The data shows that there was only a 10–20% decrease in bismuth:dimercaprol activity under anaerobic conditions. Agar diffusion studies employing strict anaerobes *Clostridium perfringens* and *Bacteroides fragilis* also suggest that bismuth:dimercaprol is minimally affected in the absence of $O_2$, possibly due to reduced solubility. Ten clinical isolates of *Helicobacter pylori* have also been tested in a microaerophilic atmosphere for sensitivity to bismuth:dimercaprol by agar diffusion. While $Bi^{3+}$ (157µg) or dimercaprol (186µg) alone produced little or no zones of inhibition, bismuth:dimercaprol (157/3 µg) typically produced zone diameters between 8 and 10 mm.

Bismuth:dimercaprol is a powerful antimicrobial agent. In comparison to either $Bi^{3+}$ or dimercaprol alone, bismuth:dimercaprol activity is orders of magnitude more potent. With few exceptions, other bismuth compounds or dimercaprol show MICs in the range of 1–10 mM, and are 100 to 1000-fold less potent than bismuth:dimercaprol. Other trivalent metals (e.g., $Al^{3+}$, $Ga^{3+}$, $Cr^{3+}$, $Ru^{3+}$, $Fe^{3+}$, $Sc^{3+}$, $y^{3+}$) when chelated with dimercaprol do not exhibit enhanced antibacterial activity.

It has also been shown that, in contrast to $Bi^{3+}$, the antibacterial effects of bismuth:dimercaprol are independent of the iron concentration. The antibacterial effects of $Bi^{3+}$ (or other trivalent metals) can be reversed by addition of micromolar amounts of iron to culture medium. However, even millimolar amounts of iron do not reverse or diminish the effects of bismuth:dimercaprol on bacteria. The lack of dependence of the bismuth:dimercaprol composition on iron concentration, as opposed to other bismuth compounds, is of therapeutic benefit in the lower gastro-intestinal tract where the conditions are anaerobic and iron is ample. Bismuth:dimercaprol has been shown to have considerable effects on gut flora, while Bismuth subsalicylate alone does not have a significant growth-inhibiting effect on these bacteria. In particular, a single bismuth:dimercaprol dose reduced the production of fecal material by 60% in rats over a 24 hour period. Feeding mice 100 µl of 1 mM or 10 mM bismuth-dimercaprol (2:1 ratio) twice daily for two weeks resulted in a 90% or 99% reduction in the number of fecal bacteria grown aerobically or anaerobically on blood agar.

It has also been found that other cations, e.g., copper, silver and gold, do have a neutralizing effect on bismuth:dimercaprol activity. In particular, copper at 78 µMneutralized the inhibitory effects of 1× and 10×, but not 100× the MIC of bismuth:dimercaprol. Therefore, these antagonists could be used to neutralize bismuth:dimercaprol when necessary.

Bismuth:dimercaprol is also able to markedly inhibit capsular polysaccharide (CPS) production. Capsular polysaccharide is produced by many bacteria for protection against desiccation and for camouflage against host defenses. Experiments were performed which showed that at 0.25 of the MIC for *Klebsiella pneumoniae,* bismuth:dimercaprol was able to inhibit 60% of the capsule expression and at less than one half of the MIC, bismuth:dimercaprol reduced the capsule expression by more than 80%, as determined by a chemical assay for sugars. In contrast, chlorhexidine (CHX), a topical agent useful as an antiseptic, a disinfectant and a preservative, had no significant effect on capsular polysaccharide expression even at 0.75 of the MIC. This reduction in capsule expression is important, since as the capsular polysaccharide surface coating is reduced, the bacteria become increasingly vulnerable to phagocytic uptake by white blood cells (WBC) in the presence of anti-capsular antiserum. It was also shown that at less than 0.5 of the MIC, the number of bacteria phagocytosed per 100 WBC increased from 19 without bismuth:dimercaprol treatment to more than 600 with bismuth:dimercaprol treatment. Although some other bismuth compounds have a similar effect on capsular polysaccharide expression and phagocytic uptake, a 100-fold higher concentration is required. Moreover, as discussed above, the addition of iron to culture media neutralizes the anti-capsular polysaccharide effect of $Bi(NO_3)_3$ or Bismuth subsalicylate, but does not effect that of bismuth:dimercaprol.

Bismuth:dimercaprol was also shown to effectively inhibit biofilm organisms. In particular, bismuth:dimercaprol was shown to be as effective against bacteria in biofilms as it is on planktonic bacteria. No other known medication has this capacity.

Bismuth:dimercaprol has strong adherence properties which should increase the safety and tolerance of the composition since bismuth:dimercaprol attaches firmly to tissue upon initial contact instead of flowing freely through the blood. In addition, these properties of bismuth:dimercaprol add to the bacterial persistence of the composition since the composition adheres tightly to the skin, the gut mucosa and other tissues, thereby providing protection for increased periods of time.

It should be understood that the bismuth:dimercaprol composition can be combined with other agents that improve its overall value or usefulness. In particular, additives, such as antioxidants, can be used with bismuth-:dimercaprol to prolong shelf-life. Antioxidants such as tocopherol have been shown to be compatible with bismuth-:dimercaprol. In addition, polycationic detergents, such as cetrimide or Zwittergent 3–14, could be added as these have been shown to improve the activity of the composition. Bismuth:dimercaprol is 100-fold more resistant to neutralization by detergents (e.g., SDS, Tween 80) than is chlorhexidine, another membrane-active biocide. Therefore, it is easier to combine bismuth:dimercaprol with soaps and detergents. Furthermore, antibiotic mixtures, antifungal, antimycobacterial or antiviral agents which increase coverage or potency can be included, particularly those against *H. pylori* which are useful against ulcerative diseases of the gastro-intestinal tract. Finally, other compounds, such as alkali, buffering agents, $H_2$-blockers, or the like that increase pH in situ and improve solubility and carrier compounds miscible with bismuth:dimercaprol that change consistency or persistence can be included. It is also contemplated that since dimercaprol has a disagreeable odor, other agents can be added to improve the taste or smell of the resulting product.

Bismuth:dimercaprol is useful for inhibiting and preventing infection by a wide variety of infectious agents and pathogens. The composition can be provided orally, intraperitoneally, intramuscularly, subdermally, intravenously, and topically. It can be provided as a liquid, powder, tablet, or a capsule. It is also contemplated that the composition can be used to coat medical devices or implants, such as catheters, or concentrated in surgical scrubs. Bismuth:dimercaprol can also be incorporated into soaps as an antibacterial agent, or used in deodorant/antiperspirants (feet or underarm use), mouthwashes, contact lens solution, cleaners, paints, food, and other perishable products. Moreover, bismuth:dimercaprol can be used to inhibit biofilm formation on industrial equipment, such as in pulp and paper manufacturing, in water towers, water filters, ventilators, air-conditioners, or incorporated in an antifouling mixture. Bismuth:dimercaprol is useful for preventing or killing biofilm populations on various devices, in swimming pools, boats, and other surfaces subjected to humid conditions. Finally, it could also be employed as a preservative or antiseptic in cosmetics or personal care products.

Although the mechanisms of action of bismuth:dimercaprol are not fully understood, it is known that the activity of bismuth:dimercaprol can not be accounted for by increased solubility alone, since the highly soluble form ($Bi^{3+}$/dimercaprol ratio=1:2) is not similar in activity to a 100-fold less soluble species (ratio=2:1). In addition, other thiol-containing chelators, namely dimercapto-succinic acid (DMSA), 2,3-dimercaptopropane-1-sulfonic acid (DMPS), and the amino acid cysteine, also solubilize bismuth as well or better than dimercaprol, but they do not increase its antibacterial properties.

Bismuth:dimercaprol has been characterized as amphipathic (amphophilic) as well as polycationic. Compounds with such properties are typically membrane-active agents; i.e., they act primarily by disrupting bacterial membranes. Electron micrographs of *E. coli* treated with 100/33.3 μM bismuth:dimercaprol support these findings. Bismuth:dimercaprol appears to concentrate in membranes. However, little or no leakage of macromolecules occurs, suggesting that bismuth:dimercaprol does not promote lysis or permeabilization. An increase in extracellular pentose shortly after bismuth:dimercaprol treatment of *E. coli* also suggests the release of nucleic acid.

It is also thought that bismuth:dimercaprol may exert its effects by inactivating membrane enzymatic activity, particularly that of membrane ATPase, by thiol exchange of $Bi^{3+}$. Capsule and slime expression is energy-intensive and is virtually shut off by bismuth:dimercaprol at subinhibitory levels; likely a result of ATPase inhibition. Being nonessential, capsular polysaccharide production can be turned off before bacterial growth is affected. Such inhibition occurs at greater than 500 μM for $Bi(NO_3)_3$, but at 5 μM for bismuth:dimercaprol. As discussed above, the marked increase in potency can not be explained by the increased solubility in water. It is instead thought the novel structure of bismuth:dimercaprol promotes permeation into bacterial membranes. Penetration through the outer membrane of gram-negative bacteria appears to be largely independent of porins and is not influenced by antibiotic afflux mechanisms. Rather, bismuth:dimercaprol penetrates the outer membrane similarly to chlorhexidine or polymyxin B; its polycationic amphophilic structure promotes an attraction to the negatively-charged, amphophilic outer membrane.

EXAMPLE 3

Antimicrobial Activity of Several Bis-thiols and Bis-nonthiols

In an effort to enhance activity by increasing solubility, bismuth was combined with several potential chelating agents. The non-thiol compounds tested were D-penicillamine, 2,2'-diaminobutyric acid, spermidine, cis 1,3-dichloropropene, EDDA, 2-Bromo-2-nitro-1, 3propanediol, salicylhydroxamic acid, sodium bisulfite, and EDTA. Tested thiols included dimercaprol (bismuth), β-mercaptoethanol (βME), 2-mercaptoethylamine (MEN), dithiothreitol (DTT), dimercaptopropane-1-sulfonic acid (DMPS), dimercaptosuccinic acid (DMSA), 1-monothioglycerol (MTG), 1,3-propanedithiol, (PDT), 3-mercapto-2-butanol (MBO), 2-mercaptopyrimidine, 2-thiouracil, 1-thioβ-D-glucose, thiosalicylic acid, thimerosal, thiolactic acid, meso-1-1'-dimercaptoadipic acid, 2,3-dimercaptopropanol tributyrate, thioglycolic acid, thiostrepton, L-cysteine, reduced glutathione, p-thiocresol, thiodiglycol, 2-mercaptobenzothiazole, pyrithione, thioanisole, 2 hydroxyethyl disulfide, 1,4-butanedithiol, 2,3-butanedithiol (BDT), 1,5-pentanedithiol, 1-pentanedithiol, 1,6-hexanedithiol, 1,2-ethanedithiol (EDT). Ethanedithiol and butanedithiol were shown to enhance bismuth activity nearly 1000 fold. The non-thiol compounds had no influence on bismuth antibacterial activity. However, the thiol chelators bismuth, propanedithiol, dithiothreitol, 3-mercapto-2-butanol, β-mercaptoethanol, 2-mercaptoehtylamine, and 1-monothioglycerol enhanced bismuth actibacterial activity by 25- to 300-fold, as measured by inhibition of *E. coli* growth (Table 5). The MICs for bismuth nitrate or thiols separately were in the low millimolar range (~3 mM), but could not be determined with precision due to their insolubility in growth media. None of the thiol acids (i.e., dimercaptopropane-1-sulfonic acid or dimercapto-succinic acid) enhanced activity whence combined with bismuth, though they exhibited similar properties in solution, such as yellow color and enhanced water solubility.

TABLE 5

Relationship between pigment intensity, lipophilicty, optimum molar ratio, and bacteriostatic concentration for several bismuth-thiol compounds

| Thiol[a] | $MIC_{2:1}$[b] | $MIC_{opt}$[c] | Optimum ratio[d] | % Bi-thiol in butanol[e] | Absorbance (410 nM)[f] | Molecular Formula |
|---|---|---|---|---|---|---|
| Dithiols | | | | | | |
| PDT | 8.6 | 12.0 | 3:1 | 58.5 ± 4.9 | 12.4 ± 0.88 | $SHCH_2CH_2CH_2SH$ |
| BAL | 12.0 | 12.0 | 2:1 | 15.5 ± 1.7 | 1.2 ± 0.23 | $OHCH_2CHSHCH_2SH$ |
| DTT | 20.9 | 10.8 | 1:1 | 2.7 ± 0.5 | 2.0 ± 0.04 | $SHCH_2(CHOH)_2CH_2SH$ |
| DMSA | 3000 | 3000 | — | 0 | 1.9 ± 0.01 | $CO_2hCHSH)_2CO_2H$ |
| Monothiols | | | | | | |
| MBO | 36.5 | 11.1 | 1:1 | 81.5 ± 0.5 | 1.0 ± 0.10 | $CH_3CHSHCHOHCH_3$ |
| δME | 98.8 | 26.7 | 1:2 | 38.3 ± 0.1 | 1.5 ± 0.01 | $CH_2OHCH_2SH$ |
| MEN | 291 | 154 | 1:3 | 8.1 ± 0.5 | 2.6 ± 0.05 | $CH_2NH_2CH_2SH$ |
| MTG | 650 | 120 | 1:4 | 8.5 ± 0.5 | 2.1 ± 0.56 | $CH_2OHCHOHCH_2SH$ |

Figure 2:
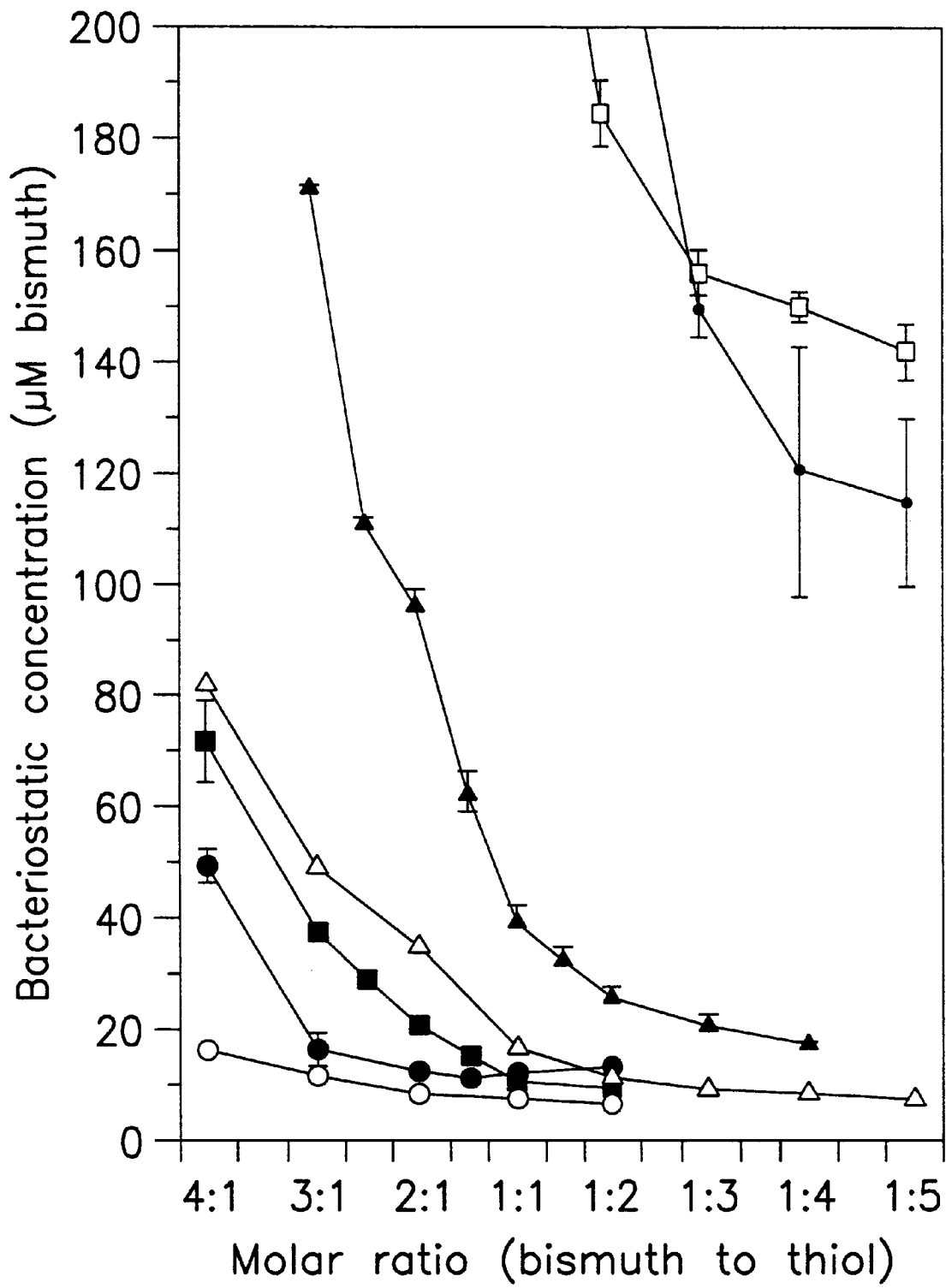
FIG. 2 shows the effect of molar ratio of bismuth to thiol compound on bismuth-thiol chelator bacteriostatic activity. Bismuth nitrate was combined with propanedithiol (○), dimercaprol (●), dithiothreitol (■); 3-mercapto-2-butanol (Δ), 2-mercaptoethylamine (□), and 1-monothioglycerol (◆) at different molar ratios and added to broth medium. Susceptibility of $E.$ $coli$ was determined in triplicate at molar ratios between 4:1 and 1:4. The bacteriostatic concentration was defined as the concentration of bismuth in combination with chelator that inhibited growth for 24±2 h. Data represents trials performed in triplicate to obtain the mean and standard deviation.

[a]PDT, 1,3,-propanedithiol; BAL 2,3,-dimercaptopropanol; DTT, 1,4-dithiothreitol;. DMSA, dimercaptosuc-cihic acid; MBO, 2-mercapto-3-butanol; δME, 2-mercaptoethanol; MEN, 2-mercaptoethylamine; MTG, 1-monothioglycerol
[b]MIC in μM bismuth against *E. coli* in broth at a 2:1 molar ratio; mean of three trials
[c]MIC against *E. coli* in at the optimum molar ratio; mean of three trials.
[d]molar ratio of bismuth:thiol producing optimum antibacterial activity
[e]% of yellow pigment from 5/10 mM bismuth-thiol solutions partitioned from $H_2O$ into butanol
[f]yellow pigment intensity of a 5/10 mM solution The seven active bismuth-thiol complexes showed optimum activity at different molar ratios. The relationship between molar ratio and MIC is illustrated in FIG. 2. The antibacterial activity of bismuth increased with increasing thiol concentrations, but reached a plateau where further addition of thiol had diminishing effects. The $MIC_{opt}$ was defined as the inhibitory concentration of bismuth at the optimum molar ratio and was essentially the optimum antibacterial activity achieved with the least amount of thiol added. The four most active bismuth-thiol compounds (bismuth:1,3-propanedithiol, bismuth:dimercaprol, bismuth:dithiothreitol, and bismuth:3-mercapto-2-butanol) produced comparably low MICs if enough thiol were added. At their respective optimum ratios, the MICs were nearly 300-fold lower than $Bi(NO_3)_3$ (MIC; ~3000 4M). However, only bismuth:1,3-propanedithiol and bismuth:dimercaprol were effective at a 3:1 ratio. The $MIC_{opt}$ for bismuth:dithiothreitol and bismuth:3-mercapto-2-butanol occurred at ratios of 1:1. The $MIC_{opt}$ for bismuth:β-mercaptoethanol occurred at a 1:2 molar ratio, twice that of bismuth:dimercaprol. Finally the $MIC_0pt$ for 2-mercaptoethylamine ad 1-monothioglycerol occurred at molar ratios of 1:3 and 1:4, respectively, and were 8-fold higher than bismuth:dimercaprol, but 25-fold lower than $Bi(NO_3)_3$.

A summary of the MIC data against *E. coli*, both at the $MIC_{opt}$ and at a 2:1 ratio, is given in Table 5. The dithiols produced the greatest synergy with bismuth, at optimum bismuth-thiol molar ratios of 3:1 to 1:1. The monothiols were generally not as synergistic, and required molar ratios of 1:1 to 1:4 for optimum antibacterial activity. There is a strong relationship between antibacterial activity and the lipophilicty of bismuth-thiol compounds, especially when monothiols and dithiols are separated. The most active bismuth-thiol in each category was also the most soluble in butanol (Table 5). Bismuth:propanedithiol and bismuth-:dimercaprol also produced the greatest yellow color in alkaline solution (Table 5), which is an indication of the amount of complex formed.

For comparison with bismuth, several trivalent metals were combined with thiol compounds and tested for antibacterial activity. Metals tested included ferric iron, aluminum (III) chloride, chromium (III) chloride, gallium (III) oxide, ruthenium red, scandium (III) oxide, yttrium (III) nitrate, and ytterbium (III) oxide. No enhanced antibacterial activity against *E. coli* was noted with dimercaprol combined with any of these metal ions at a 1:2 molar ratio. Dimercaprol enhancement of antimony or arsenic antibacterial activity was noted, but was not of the same magnitude as that of bismuth.

The stability of concentrated bismuth: dimercaprol solutions was dependent on pH, temperature, and the dimercaprol (bismuth) concentration. Bismuth:dimercaprol was stable in acidic, but not in near-neutral or basic solutions. At pH 9 the half-life of 500 μM $Bi^{3+}$/600μM dimercaprol at 25° C. was approximately 3 weeks, while that for a 500/150 μM solution was <1 week. Thus, at alkaline pH, stability depended upon the bismuth:dimercaprol molar ratio. In contrast, 2:1 bismuth:dimercaprol solutions at pH 2 exhibited no noticeable loss of activity after two months at 25° C. Bismuth:dimercaprol aqueous solutions (5 mM/2.5 mM) were stable indefinitely at pH <4, but gradually degraded at pH 6–7 ($t_{1/2}$; 1–2 weeks). Bismuth:dimercaprol solutions prepared in propylene glycol showed no loss of stability at pH values between 3 and 11.6, but the addition of 100 mM HCl destroyed activity. Autoclaving bismuth:dimercaprol solutions destroyed activity, but heating at 100° C. for 30 min had no discernable effect on activity.

Bactericidal activity increased with increasing temperature. A bismuth:dimercaprol solution of 75/37.5 μM reduced the viable *E. coli* count at 24 h by 1 log unit at 25° C., by nearly 6 log units at 35° C., and by 9 log units at 42° C. or 50° C. Bacteria incubated at these temperatures without bismuth:dimercaprol present showed no decrease in viability at 25° C. or 35° C., 1 log unit decrease at 42° C., and a 3–4 log unit decrease at 50° C.

Titrations of dimercaprol and bismuth:dimercaprol (1:2 molar ratio) with NaOH were performed. Results of the dimercaprol titration revealed two inflection regions of pH 9–10 and 10–11, corresponding to pKa values of 8.5 and 10 for the two thiol groups on dimercaprol. The solution was homogeneous and clear throughout the titration. The titration curve of bismuth:dimercaprol also revealed two inflection regions, at pH 3.5–4/5.0 (pKa; 2.9) and pH 6.0–9.0 (pKa; 5.3). In contrast to the bismuth titration, the solution was turbid with a yellow precipate, until ph 8.0, when the precipitate dissolved to form a clear yellow solution.

Figure 4:
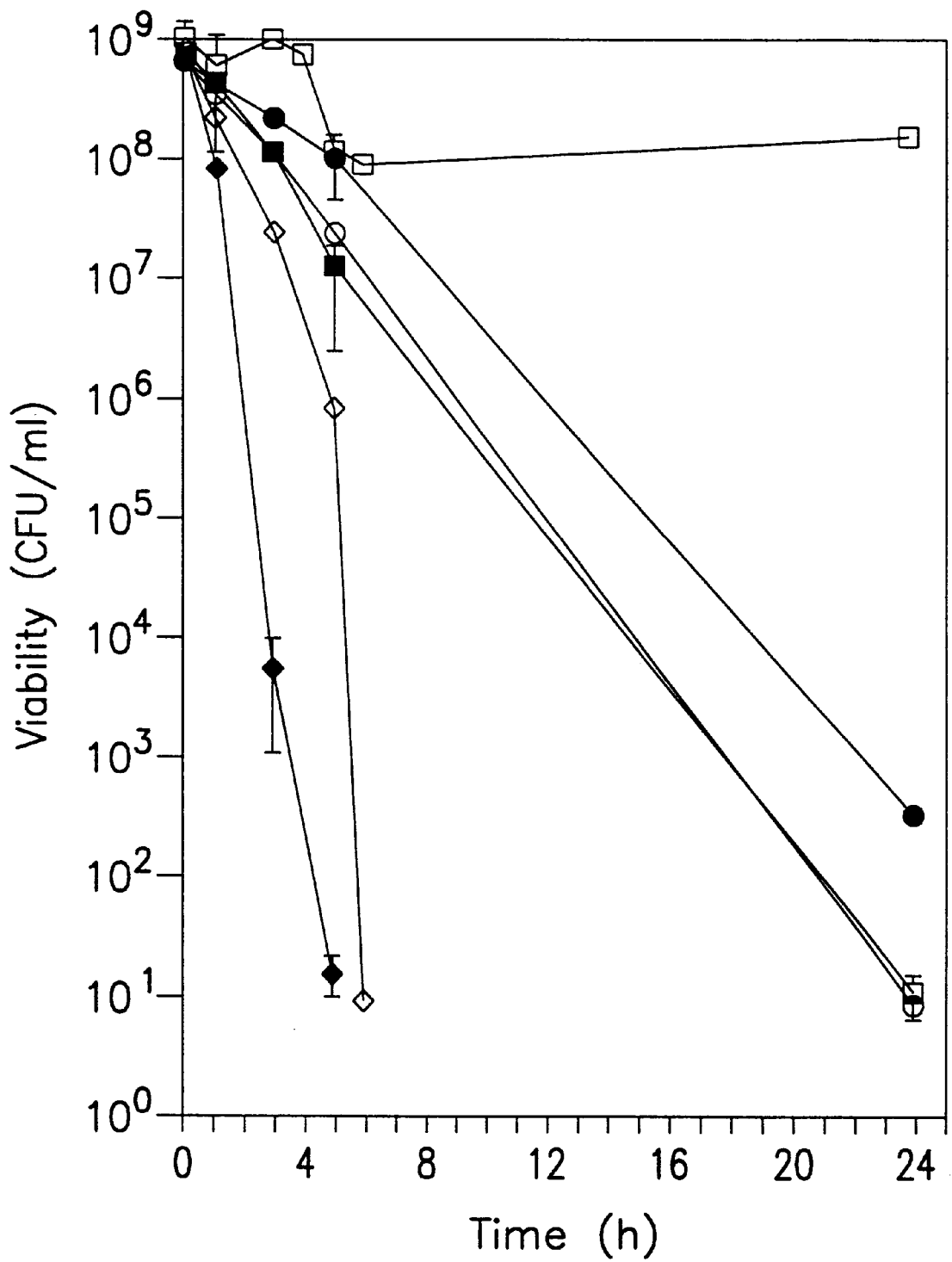
FIG. 4 shows the effect of pH on bismuth:dimercaprol bactericidal activity. $E.$ $coli$ was grown to mid-log phase in broth culture, washed once and represented in saline, and treated with 100/50 $\mu$M bismuth:dimercaprol in the presence of 10 mM buffer at pH 4 (□), pH 5(■), pH 6 (○), pH 7 (●), pH 8 (◇), and pH 9 (◆). Cultures were sampled at 1, 3, 5, and 24 h. The reduction in viability over time was determined in triplicate by standard agar plating of appropriate dilutions to obtain the mean and standard deviation.

Another pH-dependent variable was antibacterial activity (FIG. 4). Bactericidal activity against $10^9$/ml *E. coli* with 100/50 µM bismuth:dimercaprol increased progressively from pH 4.5 to 9. This follows the titration curve of bismuth:dimercaprol with NaOH and the solubility behavior of the yellow bismuth:dimercaprol precipitate. At pH 8 and 9, bactericidal activity was relatively rapid, reducing viable bacteria to near $10^1$ CFU/ml at 5 h incubation. At pH 5–7, bactericidal activity was thorough at 24 h, yet only a one or two log reduction was observed at 5 h incubation. At pH 4, no bactericidal activity above that of control values was observed, indicating that bismuth:dimercaprol is largely inactive at this pH. Subjecting *E. coli* to pH 4 or 9 without bismuth:dimercaprol present had only marginal effects on viability.

The spectrum of activity for bismuth:dimercaprol proved to be rather broad. Inhibitory and bactericidal concentrations for bismuth:dimercaprol against several medically-important bacteria are listed in Table 6. The MIC ranged from 5.9 to 63.0 µM $Bi^{3+}$ for liquid, and from 8.3 to 33.2 µg/ml powder. *E. faecalis* was most resistant to bismuth:dimercaprol. In contrast, *S. aureus* and *S. pyogenes* were 6-fold more sensitive to bismuth:dimercaprol. Bismuth:dimercaprol also inhibited the enteric gram-negative pathogens, *S. typhimurium*, enterotoxigenic *E. coli*, enterohemorrhagic (verotoxin-producing) *E. coli*, *S. flexneri*, and *Y. enterocolitica*, as well as *E. cloacae*, *K. pneumoniae*, *P. vulgaris*, and *P. aeruginosa*. bismuth:dimercaprol inhibition of several pathogens was enhanced >100-fold over that of bismuth alone. Bactericidal concentrations were 25–30% higher than the MIC. Overall only *E. faecalis* was resistant to the bactericidal activity of bismuth:dimercaprol.

TABLE 6

Susceptibility of bacteria to bismuth:dimercaprol in broth dilution

| Organism | BisBAL 2:1 Liquid (µM $Bi^{3+}$) | | BisBAL Powder (µg/ml)[a] | |
|---|---|---|---|---|
| | MIC* | MBC† | MIC* | MBC† |
| Gram-positive bacteria | | | | |
| S. aureus ATCC 25923 | 10.7 ± 1.0 | 23.1 ± 1.3 | 8.3 ± 1.7 | 18.0 ± 2.0 |
| S. pyogenes ATCC 19615 | 10.0 ± 0.9 | 36.3 ± 2.9 | NP | NP |
| E. faecalis ATCC 29212 | 63.0 ± 4.5 | >350 | 33.2 ± 3.2 | >200 |
| Gram-Negative bacteria | | | | |
| Y. enterocolitica ATCC 27729 | 5.9 ± 0.7 | 7.5 ± 0.0 | 7.7 ± 0.6 | 9.3 ± 0.6 |
| S. flexneri ATCC 12022 | 6.2 ± 0.8 | 7.0 ± 1.0 | 8.5 ± 0.7 | 10.3 ± 0.6 |
| S. typhimurium ATCC 14028 | 8.0 ± 0.8 | 10.0 ± 0.4 | 10.0 ± 1.0 | 16.7 ± 1.5 |
| E. cloacae ATCC 23355 | 9.7 ± 0.4 | 10.5 ± 0.0 | 18.4 ± 2.3 | 20.0 ± 1.8 |
| E. coli ATCC 25922 | 10.9 ± 0.3 | 11.9 ± 0.9 | 16.6 ± 1.7 | 22.0 ± 2.3 |
| K. pneumoniae ATCC 13883 | 11.0 ± 0.5 | 12.1 ± 0.3 | 18.7 ± 1.8 | 23.4 ± 1.1 |
| E. coli ATCC 35150 | 13.0 ± 0.8 | 14.7 ± 1.4 | 17.3 ± 1.6 | 19.7 ± 1.5 |
| E. coli ATCC 43896 | 14.7 ± 0.9 | 15.8 ± 0.2 | 19.8 ± 1.3 | 21.0 ± 1.0 |
| P. aeruginosa ATCC 27853 | 15.5 ± 2.3 | 28.8 ± 12.0 | 25.0 ± 2.8 | 45.0 ± 1.0 |
| P. vulgaris ATCC 13315 | 16.4 ± 4.5 | 23.5 ± 1.3 | 25.8 ± 0.5 | 28.7 ± 3.1 |

[a]Lyophilized precipitate from 1.5:1 bismuth:dimercaprol in basic aqueous solution
*MIC, drug concentration inhibiting bacterial growth for 24 h
†MBC, drug concentration reducing viability by 99.9%
NP Not performed Several bacteria were also tested for susceptibility by agar diffusion. Generally, all bacteria tested were more sensitive to bismuth:dimercaprol than to bismuth nitrate or dimercaprol alone, as demonstrated by the zones of inhibition recorded in Table 7. Among gram-positive bacteria, bismuth:dimercaprol was very effective against staphylococci, but less active against streptococci. Of 47 methicillin-resistant *S. aureus* (MRSA) isolates and 18 vancomycin-resistant enterococci (VRE), the methicillin-resistant *S. aureus* showed a partial zone of inhibition extending to 27.9±3.5 mm. No partial zones were seen for methicillin-resistant *S. aureus*. The gram-negative bacteria tested by agar diffusion included six *E. coli*, four *L. pneumophila*, and three *P. aeruginosa* isolates, all of which showed sensitivity to bismuth:dimercaprol, but very little response to its component parts.

TABLE 7

Susceptibility of bacteria to bismuth:dimercaprol in agar diffusion

| Bacteria (# of isolates) | Zones of Inhibition (mm) for: | | |
|---|---|---|---|
| | $Bi(NO_3)_3$ (157 µg) | BAL (186 µg) | BisBAL (157 µg/31 µg) |
| MRSA[a] (47) | 6.8 | 6.0 | 18.7 ± 3.1 |
| VRE[b] (18) | 6.7 | 6.0 | 10.9 ± 1.6 |
| E. coli (6) | 7.3 | 6.0 | 12.5 ± 1.3 |
| L. pneumophila (4) | 6.0 | 6.0 | 15.6 ± 1.0 |
| P. aeruginosa (3) | 6.0 | 6.0 | 16.0 ± 1.1 |

[a]Methicillin-resistant *Staphylococcus aureus*
[b]Vancomycin-resistant enterococci Bismuth:dimercaprol was also effective against *H. pylori* and anaerobic bacteria. Table 8 summarizes agar dilution studies with various clinical isolates and reference strains. Several facultative bacteria were studied in tandem under anaerobic conditions. The MICs obtained varied from 2.2 to 100 µM $Bis^{3+}$ in 1:2 ratio with dimercaprol. Bacteroides were generally more resistant than other bacteria, while *H. pylori*, *C. difficile* and *S. aureus* were most sensitive. *H. pylori* results were the average from six antibiotic-resistant isolates, including tetracycline, ampicillin, and metronidazole-resistant strains. Bismuth:dimercaprol inhibition of *E. coli* also occurred under anaerobic conditions in agar dilution studies.

TABLE 8

Agar dilution sensitivities of anaerobically-grown bacteria to bismuth:dimercaprol

| Bacterial strain | MIC ($\mu$M $Bi^{3+}$/$\mu$M BAL) |
|---|---|
| Helicobacter pylori (6 clinical isolates) | 2.2/4.4 |
| Clostridium difficile ATCC 9689 | 7.5/15 |
| Clostridium histolyticum ATCC 19401 | 22.5/45 |
| Clostridium perfringens ATCC 13124 | 50/100 |
| Bacteroides fragilis ATCC 23745 | 15/30 |
| Bacteroides ovatus ATCC 8483 | 100/200 |
| Bacteroides fragilis clinical isolate | 100/200 |
| Actinomyces odontolyticus ATCC 17929 | 22.5/45 |
| Escherichia coli ATCC 25922 | 50/100 |
| Enterococcus faecium ATCC 2358 | 50/100 |
| Staphylococcus aureus MRSA X22831 | 7.5/15 |

Figure 3:
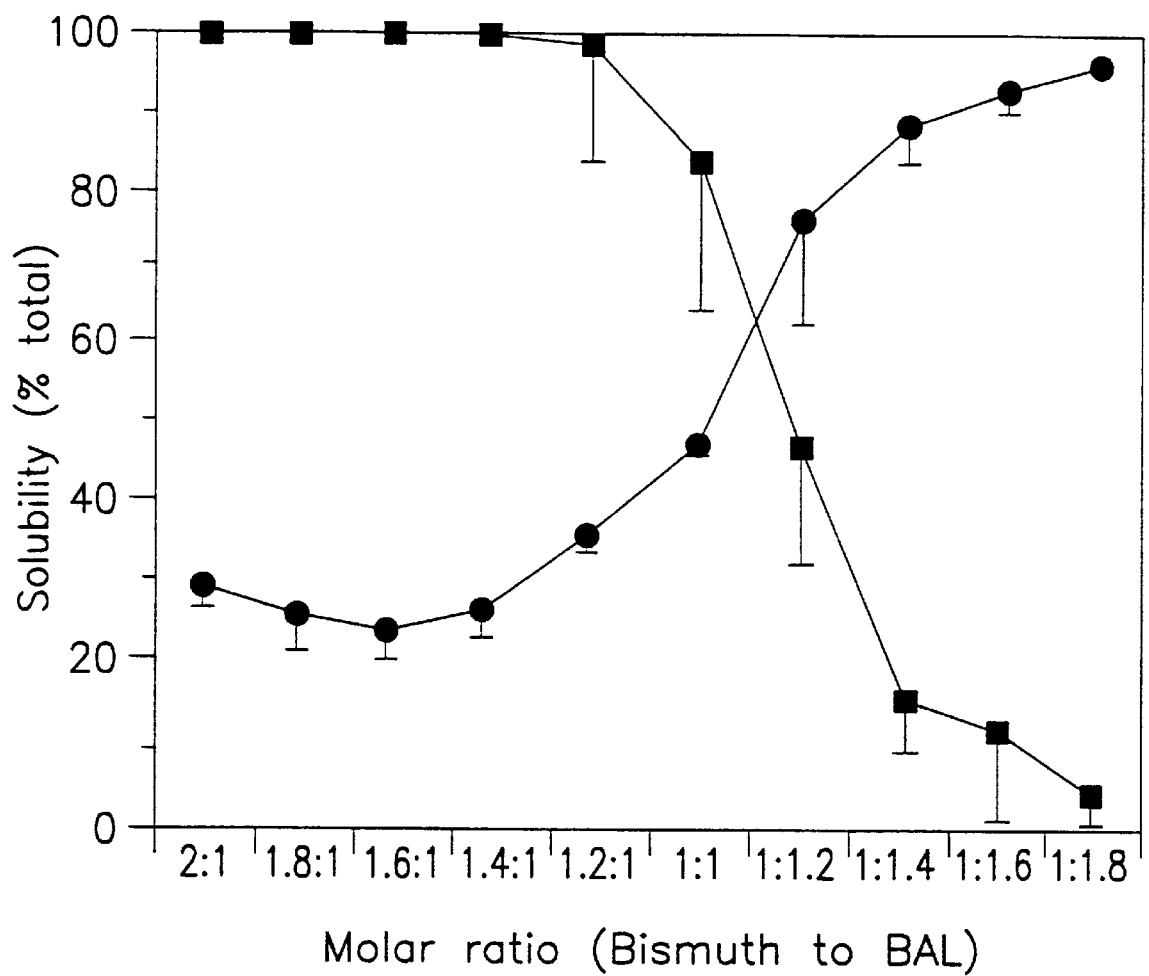
FIG. 3 shows the effect of molar ratio and pH on bismuth:dimercaprol solubility. Bismuth solutions of 5 mM in 10% propylene glycol were combined with dimercaprol at various molar ratios, either at pH 3 (■), or at pH 10 (●). The precipitate formed was sedimented, lyophilized and weighed. Percent solubility was determined by the weight of precipitate over the total weight of components added. Data represent trials performed in triplicate to obtain the mean and standard deviation.

The solubility of bismuth:dimercaprol in water was also dependent on the pH and the molar ratio, as shown in FIG. 3. At pH 10, bismuth:dimercaprol (5 mM $Bi^{3+}$) became increasingly soluble as more thiol was added, up to a 1:1.8 molar ratio. BisBAl at ratios >1.5:1 were least soluble in base, while ratios <1:1.5 were more soluble. AT pH 3, bismuth:dimercaprol (5 mM $Bi^{3+}$) became increasingly insoluble as more thiol was added, was completely soluble at 1.2:1 molar ratio in acid, and was least soluble at <1:1.5. Very slight changes in the molar ratio above or below 1:1 drastically changed the solubility in acid or base. In alkaline solutions the 1:2 form of bismuth:dimercaprol increased $Bi^{3+}$ solubility in $H_2O$ to near 500 mM, while in acid solutions the 2:1 form increased $Bi^{3+}$ solubility in propylene glycol to >50 mM $Bi^{3+}$. Other thiol compounds, such as dithiothreitol, $\beta$-mercaptoethanol, 1-monothioglycerol, dimercaptopropane-1-sulfonic acid and dimercapto-succinic acid, also significantly enhanced solubility in water in a similar fashion.

Some bismuth-thiol compounds were also soluble in 1-butanol, which was used as a measure of lipophilicty. The percentage of a 50/100 mM solution at pH 9–10 that partitioned in the butanol phase from water ranged from 2.7 to 81.5 (Table 5). The MIC correlated with lipophilicity, especially after separating the dithiols from the monothiols. Complexes containing thiols and acidic groups, such as methicillin-resistant S. aureus, dimercaptopropane-1-sulfonic acid, L-cysteine, dimercaptoadipic acid with bismuth did not exhibit synergy, while all complexes partitioning in butanol to some degree showed antibacterial synergy.

EXAMPLE 4
Antiviral Activity of Bismuth:Dimercaprol

Bismuth thiols such as bismuth:ethanedithiol or bismuth:dimercaprol are suggested for viral applications such as herpes. The infectivity titer of adenovirus, echovirus, and respiratory synetial virus was unchanged after 3 h at 37° C. with 50 $\mu$M $Bi(No_3)_3$, 25 $\mu$M dimercaprol (Bismuth-dimercaprol). However the infectivity of cytomegalovirus, herpes simplex virus type 1 (HSV-1), and HSV-2 decreased 83%, 99.2% and >99.9%, respectively. Neither $Bi(NO_3)_3$ nor dimercaprol alone had an effect. In vivo experiments consisted of topical (25 $\mu$l) and oral (100 $\mu$l) treatments of hairless mice cutaneously infected with herpes simplex virus 1. Treatments were 3 times/day for 5 days. Lesions were scored 0 to 10 (severe zosteriform ulceration). For topical treatment 8 weeks old mice were used, 10 treated with DMSO and 10 treated with 10 mM $Bi(NO_3)_3$, 5 mM dimercaprol. The control group had a PMLS of 7.5 on day 6 and 50% mortality by day 14 compared to 2.9 on day 6 and 14% mortality for the experimental group. Therefore, bismuth-dimercaprol inactives the infectivity of extracellular herpes viruses and modifies herpes simplex virus type 1 infections of mice.

EXAMPLE 5
Activities of Pyrithione Alone and in Combination with Bismuth Nitrate Against Candida Species, Cryptococcus neoformans, and Filamantous Fungi The effectiveness of pyrithione alone (in propy;ene glycol) and in combination with bismuth nitrate (bismuth nitrate:pyrithione ratio at 2:1) was investigated against Candida albcans (7 isolates) C. parapsilosis (1 isolate), C. grabrata (1 isolate), C. tropicalis (1 isolate), Cryptococcus neoformans (5 isolates), Aspergillus fumigatus (1 isolate), A. flavus (1 isolate), and Fusarium solani (1 isolate). Antifungal susceptibility testing were conducted using microbroth dilution method in RPMI broth (with L-glutamine and 3[N-morpholino]propanesulfonic acid buffer 165 mM, without sodium bicarbonate). For yeast, MICS were determined according to NCCLS (M27-T, Vol. 15 No. 10). For filamentous fungi, the proposed standardized procedure was followed (J. Clin. Microb. 1997, 35:139–143). $10^3$ CFU organisms were inoculated into wells containing serial two-fold dilutions of pyrithione alone (40 to 0.3 $\mu$M) and the combination of bismuth nitrate and pyrithione (ratio 2:1) (40/20-0.6/0.3 $\mu$M). The growth control well was drug-free, and negative control was organism-free in RPMI. The MIC microdilution plates were then incubated for 48 h (for Candida) and 72 h (for Cryptococcus and filamentous fungi) at 35° C. MIC was defined as the lowest concentration resulting a 80% inhibition of growth-control (MIC-2) and a concentration preventing any discernible growth (MIC-0). The minimal fungicidal concentrations (MFC) of pyrithione alone and in combination with bismuth nitrate were determined by plating 100 $\mu$l samples from each well onto Sabouraud dextrose agar. MFC was defined as the lowest concentration causing a 90% reduction in the number of CFUs of the initial inoculum after 24 h incubation.

Pyrithione against 7 isolates of C. albicans had MIC-2 range (a concentration resulting 80% inhibition of growth control) from 0.6–2.5 $\mu$M and had MFC range (a concentration resulting 99% killing of initial inoculum) of 2.5–20 $\mu$M. Bismuth nitrate had only limited activity against C. albicans with MIC-2 80 $\mu$M or greater. When bismuth nitrate was combined with pyrithione, the MIC-2 range (Bismuth/pyrithione 2:1) was from 2.5/1.25 to 10/5 $\mu$M Table 9). The combined MIC-2 and MFC of pyrithione were identical to or ±1–2 dilution changes than those of pyrithione alone. An unusual phenomenon was found that was a much higher MICs-0 (a concentration resulting invisible growth) of pyrithione alone ($\geq$40 $\mu$M) in 5 of 7 tested strains of C. albicans than their MFCs (2.5–10$\mu$M). These results were repeated three times. This phenomenon might be caused by a slow process of killing or a severe inhibition. Organisms that phenomenon might be caused by a slow process of killing or a severe inhibition. Organisms grew at the first few hours during the incubation, but they were unable regrowth within 24–48 h even in the drug-free medium. However, when pyrithione combined with bismuth nitrate, they inhibitory activity might act promptly and showed a fungicidal activity, because the most combined minimal fungicidal concentrations showed identical to their MICs-0. Synergy between bismuth and pyrithione was found (four-fold reduction of MIC or minimal fungicidal concentration) against C. parapsilosis, C. tropicalis, and C. glabrata. However, there were no antifungal activity against C. krusei (Table 9).

TABLE 9

MICs and MFCs of pyrithione alone and combination
with bismuth nitrate against Candida species

| | Pyrithione alone (μM) | | | Bismuth nitrate[a]/ Pyrithione (μM) | | |
|---|---|---|---|---|---|---|
| Organism | MIC-2 | MIC-0 | MFC | MIC-2 | MIC-0 | MFC |
| C. albicans 96-14[b] | 2.5 | 10 | 20 | 10/5 | 10/5 | >40/20 |
| C. albicans 96-99 | 1.25 | 1.25 | 2.5 | 2.5/1.25 | 2.5/1.25 | 5/2.5 |
| C. albicans Y537 | 1.25 | >40 | 2.5* | 5/2.5 | 10/5 | 10/5 |
| C. albicans MY1012 | 20 | 40 | 40 | 10/5 | 20/10 | 40/20 |
| C. albicans 96-95 | 0.6 | >40 | 10* | 10/5 | 5/2.5 | 20/10 |
| C. albicans 96-59 | 1.25 | >40 | 5* | 10/5 | 10/5 | 10/5 |
| C. albicans 96-66 | 0.6 | 40 | 5* | 2.5/1.25 | 5/2.5 | 5/2.5 |
| C. albicans 96-79 | 2.5 | >40 | 2.5* | 10/5 | 10/5 | 10/5 |
| C. parasilosis 96-101 | 2.5 | >40 | >40 | 10/5 | 20/10 | >40/20 |
| C. grabrata 96-91 | 2.5 | >40 | >40 | 20/10 | 40/20 | >40/20 |
| C. tropicalis 96-54 | 2.5 | >40 | 40 | 5/2.5 | 10/5 | 40/20 |
| C. Krusei 96-101 | >40 | >40 | >40 | >40/20 | >40/20 | >40/20 |

[a]MICs of Bismuth nitrate in propylene glycerol were ≧80 μM
*MICs and MFCs of pyrithione were repeated three times.

Pyrithione alone and in combination against *C. neofoormans* showed moderate inhibitory activities (Table 10). Again bismuth nitrate had limited activity, with MIC-2>80 μM. The combination of bismuth nitrate and pyrithione showed additive (4 strains) and indifferent effect (1 strain).

TABLE 10

MICs and MFCs pyrithione alone and in combination
with bismuth nitrate against Cryptococcus neoformans

| | Pyrithione alone (μM) | | | Bismuth nitrate[a]/ Pyrithione (μM) | | |
|---|---|---|---|---|---|---|
| Organism | MIC-2 | MIC-0 | MFC | MIC-2 | MIC-0 | MFC |
| C. neoformans 95-116 | 40 | >40 | >40 | 20/10 | 40/20 | 40/20 |
| C. neoformans 96-93 | 2.5 | 2.5 | 2.5 | 5/2.5 | 10/5 | 10/5 |
| C. neoformans 97-55 | 20 | 20 | 20 | 5/2.5 | 10/5 | 10/5 |
| C. neoformans 96-77 | 20 | 40 | 40 | 20/10 | 20/10 | 40/20 |
| C. neoformans 96-84 | 20 | 40 | 40 | 20/10 | 40/20 | 40/20 |

The results shown in Table 11 reveal that *Aspergillus fumigatus*, *A. flavus* and *Fusarium solani* were resistant to both pyrithione alone and in combination with bismuth nitrate.

TABLE 11

In vitro activities of pyrithione alone
and in combination with bismuth nitrate
against Aspergillus and Fusanium species

| | Pyrithione alone (μM) | | Bismuth nitrate[a]/ Pyrithione (μM) | |
|---|---|---|---|---|
| Organism | MIC-2 | MIC-0 | MIC-2 | MIC-0 |
| A. fumigatus 6 | >40 | >40 | >40/>20 | >40/>20 |
| A. flavus 2 | >40 | >40 | >40/>20 | >40/>20 |
| Fusarium solani 18 | >40 | >40 | >40/>20 | >40/>20 |

Experimental Evidence of Effectiveness of the Invention

Effectiveness in killing different bacteria. The $MIC_{90}$ for bismuth:ethanedithiol against methicillin-resistant *Staphylococcus epidermidis* is 1.63 μM $Bi^{3+}$. Against *S. epidermidis* reference strain (ATCC 12228), the MIC was 0.09 μM. *Staphylococcus aureus* ATCC 25923 was sensitive at 2.1 μM. virtually all bacteria, including very resistant pathogens, are sensitive to bismuth:ethanedithiol at ≦5.2 μM. The vancomycin-resistant enterococci and group B streptococci are slightly more resistant, with MICs as high as 15 μM bismuth:ethanedithiol.

Retardation of bacterial growth. Hydrogel catheters coated with bismuth:dimercaprol (50/75 mM) retarded bacterial growth for several weeks. Coated catheters were implanted daily into fresh agar seeded with bacteria. Catheters retarded the growth of *Escherichia coli* for 20 days, and was still producing a zone of inhibited of 31 mm against a slime-forming *S. epidermidis* after 40 days. Thus, dipping hydrogel-coated plastics in bismuth-thiols provided an antibacterial coating that releases slowly into aqueous environments. Coatings last 3 weeks or more against different bacteria.

Effectiveness of Bismuth-thiols as anti-biofilm agents. Bismuth-thiols (BTs) are useful for combating biofilms in both medicine and industry. Several bismuth:thiols have been discovered thus far, each with different qualities and potencies. The advantages for bismuth-thiols in antibiofilm action are:

1) Effectiveness at relatively low concentrations. Bismuth-dimercaprol at 10 μM inhibits biofilm formation by Pseudomonas, Bacillus, Acidovorax, or Vibrio spp. for weeks at a time. Capsule and slime expression from Klebsiella or Pseudomonas was virtually eliminated at 5 μM Bi in Bismuth-dimercaprol. The results show that only 2 ppm (10 μM) Bismuth-dimercaprol is required to prevent biofilms vs. 5 ppm of chlorine for same purposes. Furthermore, bismuth:ethanedithiol is 5-fold better than bismuth:dimercaprol.

2) Prevention of biofilm formation. Biofilm by slime-producing bacteria (Pseudomonas, Acidovorax, Bacillus, Vibrio spp.) was prevented by >90% over 15 days with bismuth:dimercaprol (1–10 μM $Bi^{3+}$). Bismuth:dimercaprol also prevented biofilm from the marine bacterium Hyphomonas at 25 μM $Bi^{3+}$.

3) Inhibition of capsule and slime formation. Klebsiella capsule expression was inhibited >90% by bismuth:dimercaprol at 5 μM $Bi^{3+}$. Pseudomonas alginate expression was inhibited >90% by bismuth:dimercaprol at 2.5 μM $Bi^{3+}$.

4) Equal effectiveness against pre-formed biofilm as against planktonic organisms. Biofilms are usually 50–500-fold more resistant to antibiotic killing than planktonic organisms, but for bismuth:dimercaprol, MBC planktonic is about the same as MBC biofilm. Cationic lipophilic agents are believed to be able to penetrate to the heart of biofilm and kill sessile organisms. Bismuth:dimercaprol appears to kill bacteria without lysing or permeabilizing them, thus not feeding other bacteria deeper in the biofilm.

Accordingly, the present invention provides a method of preventing the formation or growth of biofilms, comprising the step of applying to an area on which it is desired to prevent the formation or growth of biofilms an effective amount of a composition comprising a metal chelated by a thiol compound in the form a metal:thiol complex, wherein said metal is selected from the group consisting of bismuth, arsenic and antimony.

Although the present invention has been described in relation to particular embodiments thereof, many other variations and modifications and other uses will become apparent to those skilled in the art. It is preferred, therefore, that the present invention be limited not by the specific disclosure herein, but only by the appended claims.

What is claimed is:

1. A method of suppressing bacterial growth comprising the step of supplying to a region for which said suppression is desired, an anti-bacterial agent comprising an antibacterial formulation selected from the group consisting of:

(A) a mixture comprising (i) a non-pyrithione complexing agent having at least one thiol group, and (ii) bismuth or a bismuth containing compound;

(B) a complex whose molecular structure includes (i) a non-pyrithione complexing agent having at least one thiol group, (ii) bismuth or a bismuth-containing compound; and (iii) a coordinate bond linking at least one sulfur atom of the thiol-containing complexing agent of subparagraph (B) (i) to the bismuth of subparagraph (B)(ii); and (C) a combination comprising the complex of paragraph (B) and at least one specie selected from the group consisting of (i) a thiol-containing complexing agent and (ii) bismuth or a bismuth-containing compound;

wherein the molar ratio of bismuth to thiol-containing complexing agent in said anti-bacterial formulation is between 1:2 and 3:1.

2. The method of claim 1, wherein the molar ratio of bismuth to thiol-containing complexing agent in said anti-bacterial formulation is between 1:1 and 3:1.

3. The method of claim 1, wherein the molar ratio of bismuth to thiol-containing complexing agent in said anti-bacterial formulation is between 2:1 and 3:1.

4. The method of claim 1, wherein the thiol-containing complexing agent of each of paragraphs (A), (B) and (C) has, in its molecular structure, at least two sulfhydryl groups.

5. The method of claim 4, wherein one sulfhydryl group is bound to a first carbon atom and another sulfhydryl group is bound to a second carbon atom, and wherein said first carbon atom is separated from said second carbon atom by 0–3 intervening atoms.

6. The method of claim 5, wherein said first carbon atom is separated from said second carbon atom by 0–1 intervening atoms.

7. The method of claim 1, wherein a 5:10 mM solution of said bismuth:thiol-containing complexing agent has a light absorbance of at least 1.5 at a wavelength of 410 nanometers.

8. The method of claim 7, wherein said 5:10 mM solution of said bismuth:thiol-containing complexing agent has a light absorbance of at least 10 at a wavelength of 410 nanometers.

9. The method of claim 7, wherein at least 10% of said complex partitions from water into butanol when partitioned using equal volumes of water and butanol at 25° C. and a 5:10 mM solution of said bismuth to complexing agent, respectively.

10. The method of claim 1, wherein at least 1% of said complex partitions from water into butanol when partitioned using equal volumes of water and butanol at 25° C. and a 5:10 mM solution of said bismuth to complexing agent, respectively.

11. The method of claim 1, wherein at least 10% of said complex partitions from water into butanol when partitioned using equal volumes of water and butanol at 25° C. and a 5:10 mM solution of said bismuth to complexing agent, respectively.

12. The method of claim 1, wherein the thiol-containing complexing agent of each of paragraphs (A), (B) and (C) is selected from the group consisting of 3,4-dimercaptotoluene, trithiocyanuric acid, 2,5-dimercapto-1,3,4-thiadiazole, 2,3-dimercapto-1-propanol, 2-mercapto-3-butanol, β-mercaptoethanol, 2-mercaptoethylamine, 1-monothioglycerol, ethanedithiol, 2,3-butanedithiol, 1,4-butanedithiol, 1,4-dimercapto-2,3-butanediol, 1,2-propanedithiol, and 1,3-propanedithiol.

13. The method of claim 1, wherein the thiol-containing complexing agent is 1,3-propanedithiol and said antibacterial agent is in solution at a pH of less than 5.0.

14. The method of claim 1, wherein the thiol-containing complexing agent is 1,3-propanedithiol and said antibacterial agent is in solution at a pH no higher than 3.0.

15. The method of claim 1, wherein said bacteria are mycobacteria.

16. The method of claim 1, wherein said method further comprises applying an anti-fungal agent to said region where suppression of bacterial growth is desired.

17. A method of suppressing bacterial growth comprising the step of supplying to a region for which said suppression is desired at least one anti-microbial agent comprising an antimicrobial formulation selected from the group consisting of:

(A) a mixture comprising a di-thiol complexing agent and bismuth or a bismuth-containing compound;

(B) a complex whose molecular structure includes (i) a di-thiol complexing agent, (ii) bismuth or a bismuth-containing compound, and (iii) a coordinate bond linking at least one sulfur atom of the thiol-containing complexing agent to bismuth; and (C) a combination comprising the complex of paragraph (B) and at least one specie selected from the group consisting of (i) a di-thiol complexing agent and (ii) bismuth or a bismuth-containing compound;

wherein the molar ratio of bismuth to di-thiol complexing agent in said anti-microbial formulation is between 1:2 and 3:1;

wherein the di-thiol complexing agent of each of paragraphs (A), (B) and (C) has one thiol group bound to a first carbon atom and another thiol group bound to a second carbon atom, and wherein said first carbon atom is separated from said second carbon atom by 0–3 intervening atoms;

wherein a 5:10 mM solution of said bismuth:complexing agent has a light absorbance of at least 1.5 at a wavelength of 410 nanometers; and wherein at least 1% of said complex partitions from water into butanol when partitioning tests are run using equal volumes of water and butanol at 25° C. and a 5:10 mM solution of said bismuth to said complexing agent, respectively.

18. A method of reducing bacterial infestation comprising the step of supplying to a region where said reduction is desired an anti-bacterial agent comprising an antibacterial formulation selected from the group consisting of:

(A) a mixture comprising (i) a non-pyrithione complexing agent having at least one thiol group, and (ii) bismuth or a bismuth-containing compound;

(B) a complex whose molecular structure includes (i) a non-pyrithione complexing agent having at least one thiol group, (ii) bismuth or a bismuth-containing compound; and (iii) a coordinate bond linking at least one sulfur atom of the thiol-containing complexing agent of subparagraph (B) (i) to the bismuth of subparagraph (B)(ii); and (C) a combination comprising the complex of paragraph (B) and at least one specie selected from the group consisting of (i) a thiol-containing complexing agent and (ii) bismuth or a bismuth-containing compound;

wherein the molar ratio of bismuth to thiol-containing complexing agent in said anti-bacterial formulation is between 1:2 and 3:1.

19. The method of claim 18, wherein said method further comprises applying an antifungal agent to said region where reduction of bacterial infestation is desired.

20. A method of treating, or suppressing the acquisition of, bacterial infection comprising the step of administering to a patient in need of said treatment or suppression, an effective amount of an anti-bacterial agent comprising an antibacterial formulation selected from the group consisting of:

(A) a mixture comprising (i) a non-pyrithione complexing agent having at least one thiol group, and (ii) bismuth or a bismuth-containing compound;

(B) a complex whose molecular structure includes (i) a non-pyrithione complexing agent having at least one thiol group, (ii) bismuth or a bismuth-containing compound; and (iii) a coordinate bond linking at least one sulfur atom of the thiol-containing complexing agent of subparagraph (B) (i) to the bismuth of subparagraph (B)(ii); and (C) a combination comprising the complex of paragraph (B) and at least one specie selected from the group consisting of (i) a thiol-containing complexing agent and (ii) bismuth or a bismuth-containing compound;

wherein the molar ratio of bismuth to thiol-containing complexing agent in said anti-bacterial formulation is between 1:2 and 3:1.

21. The method of claim 20, wherein said bacteria are mycobacteria.

22. The method of claim 20, wherein said bacteria are gram negative bacteria.

23. The method of claim 20, wherein said bacteria are selected from the group consisting of Pseudomonas and Klebsiella.

24. The method of claim 20, wherein said anti-bacterial agent is supplied at a sub-lethal dosage.

25. A method of reducing biofilm comprising the step of contacting biofilm with an anti-microbial agent comprising an antimicrobial formulation selected from the group consisting of:

(A) a mixture comprising (i) a complexing agent having at least one thiol group, and (ii) bismuth or a bismuth-containing compound;

(B) a complex whose molecular structure includes (i) a non-pyrithione complexing agent having at least one thiol group, (ii) bismuth or a bismuth-containing compound; and (iii) a coordinate bond linking at least one sulfur atom of the thiol-containing complexing agent of subparagraph (B)(i) to the bismuth of subparagraph (B)(ii); and (C) a combination comprising the complex of paragraph (B) and at least one specie selected from the group consisting of (i) a thiol-containing complexing agent and (ii) bismuth or a bismuth-containing compound.

26. The method of claim 25, wherein said biofilm comprises bacteria.

27. The method of claim 25, wherein at least one complexing agent lacks oxygen in its molecular structure.

28. A method of preventing the conversion of bacteria into biofilm comprising the step of contacting said bacteria with a biofilm suppressing agent comprising an antimicrobial selected from the group consisting of:

(A) a mixture comprising (i) a complexing agent having at least one thiol group, and (ii) bismuth or a bismuth-containing compound;

(B) a complex whose molecular structure includes (i) a complexing agent having at least one thiol group, (ii) bismuth or a bismuth-containing compound; and (iii) a coordinate bond linking at least one sulfur atom of the thiol-containing complexing agent of subparagraph (B) (i) to the bismuth of subparagraph (B)(ii); and (C) a combination comprising the complex of paragraph (B) and at least one specie selected from the group consisting of (i) a thiol-containing complexing agent and (ii) bismuth or a bismuth-containing compound.

29. The method of claim 28, wherein said biofilm comprises bacteria.

30. The method of claim 28, wherein said bacteria are contacted with a sub-lethal amount of said anti-microbial.

31. The method of claim 28, wherein at least one complexing agent lacks oxygen in its molecular structure.

32. A method of reducing bacterial secretion of exopolysaccharides comprising the step of contacting bacteria for which said reduction is desired with an anti-microbial agent comprising an antimicrobial formulation selected from the group consisting of:

(A) a mixture comprising (i) a complexing agent having at least one thiol group, and (ii) bismuth or a bismuth-containing compound;

(B) a complex whose molecular structure includes (i) a complexing agent having at least one thiol group, (ii) bismuth or a bismuth-containing compound; and (iii) a coordinate bond linking at least one sulfur atom of the thiol-containing complexing agent of (B) (i) to the bismuth of subparagraph (B)(ii); and (C) a combination comprising the complex of paragraph (B) and at least one specie selected from the group consisting of (i) a thiol-containing complexing agent and (ii) bismuth or a bismuth-containing compound (antimony and arsenic.

33. The method of claim 32, wherein at least one complexing agent lacks oxygen in its molecular structure.

34. A method of preventing spoilage, comprising the step of:

applying to a product on which it is desired to prevent spoilage an effective amount of anti-microbial agent comprising an antimicrobial formulation selected from the group consisting of:
- (A) a mixture comprising (i) a complexing agent having at least one thiol group, and (ii) bismuth or a bismuth-containing compound;
- (B) a complex whose molecular structure includes (i) a complexing agent having at least one thiol group, (ii) bismuth or a bismuth-containing compound; and (iii) a coordinate bond linking at least one sulfur atom of the thiol-containing complexing agent of subparagraph (B) (i) to the bismuth of subparagraph (B)(ii); and
- (C) a combination comprising the complex of paragraph (B) and at least one specie selected from the group consisting of (i) a thiol-containing complexing agent and (ii) bismuth or a bismuth-containing compound;
  wherein the molar ratio of bismuth to thiol-containing complexing agent in said anti-bacterial formulation is between 1:2 and 3:1.

35. The method of claim 34, wherein at least one complexing agent lacks oxygen in its molecular structure.

36. A method of suppressing the conversion of bacteria to biofilm without eradicating said bacteria, said method comprising the step of contacting said bacteria with a sub-lethal amount of a biofilm preventative agent comprising a formulation selected from the group consisting of:
- (A) A mixture of (i) a pyrithione complexing agent, and (ii) bismuth or a bismuth-containing compound;
- (B) a complex whose molecular structure includes (i) a pyrithione complexing agent, and (i) bismuth or a bismuth-containing compound; and (iii) at least one coordinate bond linking said pyrithione complexing agent of subparagraph (B)(i) to the bismuth of subparagraph (B)(ii); and
- (C) a combination of the complex of paragraph (B) and at least one species selected from the group consisting of (i) a pyrithione complexing agent and (ii) bismuth or a bismuth-containing compound.

37. The method of claim 36, wherein said method further comprises applying an antifungal agent to a region where suppression of the conversion of said bacteria to biofilm is desired.

38. A method of reducing biofilm comprising the step of contacting biofilm with an antimicrobial agent comprising an antimicrobial formulation selected from the group consisting of:
- (A) A mixture of (i) a pyrithione complexing agent, and (ii) bismuth or a bismuth-containing compound;
- (B) a complex whose molecular structure includes (i) a pyrithione complexing agent, and (i) bismuth or a bismuth-containing compound; and (iii) at least one coordinate bond linking said pyrithione complexing agent of subparagraph (B)(i) to bismuth of subparagraph (B)(ii); and
- (C) a combination of the complex of paragraph (B) and at least one species selected from the group consisting of (i) a pyrithione complexing agent and (ii) bismuth or a bismuth-containing compound .

39. The method of claim 38, wherein said biofilm comprises bacteria.

40. A method of treating products to improve the resistance of said product to microbial infestation comprising treating said product with an antimicrobial agent comprising an antimicrobial formulation selected from the group consisting of:
- (A) a mixture comprising (i) a non-pyrithione complexing agent having at least one thiol group, and (ii) bismuth or a bismuth-containing compound;
- (B) a complex whose molecular structure includes (i) a non-pyrithione complexing agent having at least one thiol group, (ii) bismuth or a bismuth-containing compound; and (iii) a coordinate bond linking at least one sulfur atom of the thiol-containing complexing agent of subparagraph (B) (i) to the bismuth of subparagraph (B)(ii); and
- (C) a combination comprising the complex of paragraph (B) and at least one specie selected from the group consisting of (i) a non-pyrithione thiol-containing complexing agent and (ii) bismuth or a bismuth-containing compound;
  wherein the molar ratio of bismuth to thiol-containing complexing agent in said anti-bacterial formulation is between 1:2 and 3:1.

41. An antimicrobial agent comprising an antimicrobial formulation selected from the group consisting of:
- (A) a mixture comprising (i) a complexing agent having at least one thiol group and no oxygen in its molecular structure, and (ii) bismuth or a bismuth-containing compound;
- (B) a complex whose molecular structure includes (i) a complexing agent having at least one thiol group and no oxygen in its molecular structure, (ii) bismuth or a bismuth-containing compound; and (iii) a coordinate bond linking at least one sulfur atom of the thiol-containing complexing agent of subparagraph (B) (i) to the bismuth of subparagraph (B)(ii); and
- (C) a combination comprising the complex of paragraph (B) and at least one specie selected from the group consisting of (i) a thiol-containing complexing agent with no oxygen in its molecular structure and (ii) bismuth or a bismuth-containing compound, wherein said antimicrobial agent has at least one of the following characteristics:
  (1) it is in a powder form;
  (2) the antimicrobial formulation is in solution and the solution pH is below 7.0;
  (3) the antimicrobial formulation is in an alcohol-containing solution;
  (4) at least 1% of said complex partitions from water into butanol when partitioned using equal volumes of water and butanol at 25° C. and a 5:10 mM solution of said bismuth to said complexing agent, respectively; or
  (5) a 5 mM solution of said bismuth and a 10 mM solution of thiol-containing complexing agent has a light absorbance of at least 1.5 at a wavelength of 410 nanometers.

* * * * *